(12) United States Patent
Scarcelli et al.

(10) Patent No.: US 10,598,594 B2
(45) Date of Patent: Mar. 24, 2020

(54) CELL CLASSIFICATION BASED ON MECHANICAL SIGNATURE OF NUCLEUS

(71) Applicants: University of Maryland, College Park, College Park, MD (US); Canon U.S.A., Inc., Melville, NY (US)

(72) Inventors: Giuliano Scarcelli, College Park, MD (US); Jitao Zhang, College Park, MD (US); Hanyoup Kim, Newport News, VA (US)

(73) Assignees: University of Maryland, College Park, MD (US); Canon U.S.A., Inc., Melville, NY (US)

( * ) Notice: Subject to any disclaimer, the term of this patent is extended or adjusted under 35 U.S.C. 154(b) by 0 days.

(21) Appl. No.: 15/909,699

(22) Filed: Mar. 1, 2018

(65) Prior Publication Data
US 2018/0188173 A1 Jul. 5, 2018

Related U.S. Application Data

(63) Continuation-in-part of application No. 15/388,582, filed on Dec. 22, 2016.
(Continued)

(51) Int. Cl.
*G01N 21/00* (2006.01)
*G01N 21/63* (2006.01)
(Continued)

(52) U.S. Cl.
CPC ......... *G01N 21/636* (2013.01); *G01N 15/147* (2013.01); *G01N 15/1429* (2013.01); *G01N 15/1434* (2013.01); *G01N 15/1463* (2013.01); *G01N 2015/1006* (2013.01); *G01N 2015/1488* (2013.01); *G01N 2021/638* (2013.01); *G01N 2800/7028* (2013.01); *H01S 3/307* (2013.01)

(58) Field of Classification Search
CPC ... H01J 37/32935; G01N 21/64; G01N 21/68; G01N 2015/1037; G01J 3/02
USPC .......................................................... 356/72
See application file for complete search history.

(56) References Cited

U.S. PATENT DOCUMENTS

| 6,002,480 A | 12/1999 | Izatt et al. |
| 8,115,919 B2 | 2/2012 | Yun et al. |
(Continued)

FOREIGN PATENT DOCUMENTS

| CN | 1212021 A | 3/1999 |
| EP | 0 497 788 B1 | 4/1997 |
(Continued)

OTHER PUBLICATIONS

Zhang, Jitao et al., "Brillouin flow cytometry for label-free mechanical phenotyping of the nucleus," Lab on a Chip, vol. 17, No. 4, pp. 663-670 (2017).
(Continued)

*Primary Examiner* — Md M Rahman
(74) *Attorney, Agent, or Firm* — Rothwell, Figg, Ernst & Manbeck, P.C.

(57) ABSTRACT

The present invention relates to a method and system for identifying mechanical properties of a cell nucleus through a label-free cell analysis based on Brillouin light scattering techniques. The present application additionally provides a method and system for identifying cancerous cells based on mechanical properties of the cell nucleus.

23 Claims, 20 Drawing Sheets

Related U.S. Application Data

(60) Provisional application No. 62/270,982, filed on Dec. 22, 2015, provisional application No. 62/339,512, filed on May 20, 2016, provisional application No. 62/323,176, filed on Apr. 15, 2016, provisional application No. 62/425,070, filed on Nov. 21, 2016, provisional application No. 62/465,230, filed on Mar. 1, 2017.

(51) Int. Cl.
*G01N 15/14* (2006.01)
*H01S 3/30* (2006.01)
*G01N 15/10* (2006.01)

(56) References Cited

U.S. PATENT DOCUMENTS

| | | | |
|---|---|---|---|
| 2003/0113821 | A1 | 6/2003 | Yagita |
| 2009/0323056 | A1 | 12/2009 | Yun et al. |
| 2011/0065741 | A1* | 3/2011 | Forbes ............. A61K 31/437 514/281 |
| 2011/0164783 | A1 | 7/2011 | Hays et al. |
| 2012/0129189 | A1* | 5/2012 | Kwon ............. C12N 5/0606 435/7.21 |
| 2012/0274937 | A1 | 11/2012 | Hays et al. |
| 2012/0302862 | A1 | 11/2012 | Yun et al. |
| 2014/0368792 | A1 | 12/2014 | Friedman et al. |
| 2015/0022781 | A1 | 1/2015 | Wada et al. |
| 2016/0151202 | A1 | 6/2016 | Scarcelli et al. |
| 2017/0165506 | A1 | 6/2017 | Ortiz et al. |

FOREIGN PATENT DOCUMENTS

| | | |
|---|---|---|
| WO | 97/27331 A2 | 7/1997 |
| WO | 2015/051854 A1 | 4/2015 |
| WO | 2015/135415 A1 | 9/2015 |
| WO | 2017/053592 A1 | 3/2017 |

OTHER PUBLICATIONS

Antonacci, Giuseppe et al., "Biomechanics of subcellular structures by non-invasive Brillouin microscopy," Scientific Reports, vol. 6, No. 37217, pp. 1-7 (2016).
Scarcelli G and Yun S H, "Confocal Brillouin microscopy for three-dimensional mechanical imaging", Nature Photonics 2, 39-43 (2007).
Berghaus K, Zhang J, Yun SH, Scarcelli G, "High-finesse sub-GHz-resolution spectrometer employing VIPA etalons of different dispersion", Opt. Lett. 40, 4436-4439 (2015).
Fiore A, Zhang J, Shao P, Yun SH, Scarcelli G, "High-extinction virtually imaged phased array-based Brillouin spectroscopy of turbid biological media", Appl Phys Lett. 108, 203701 (2016).
Girard M J A, Dupps W J, Baskaran M, Scarcelli G, Yun S H, Quigley HA, Sigal I A and Strouthidis N G, "Translating Ocular Biomechanics into Clinical Practice: Current State and Future Prospects", Curr. Eye Res. 40(1), 1-18 (2015).
Scarcelli, G., Kim, P. & Yun, S.H. "In vivo measurement of age-related stiffening in the crystalline lens by Brillouin Optical microscopy", Biophysical Journal 101, 1539-1545 (2011).
Scarcelli, G. & Yun, S.H. "In vivo Brillouin optical microscopy of the human eye", Optics Express 20, 9197 (2012).
Kim, M. et al. "Shear Brillouin light scattering microscope," Opt. Express. 24, 319-328 (2016).
Scarcelli G, Polacheck WJ, Nia HT, Patel K, Grodzinsky AJ, Kamm RD, Yun SH, "Noncontact three-dimensional mapping of intracellular hydromechanical properties by Brillouin microscopy", Nat Methods. 12, 1132-1134 (2015).
Ingber DE, Wang N, Stamenovic D, "Tensegrity, cellular biophysics, and the mechanics of living systems", Rep Prog Phys. 77, 046603 (2014).
Wakatsuki T, Schwab B, Thompson NC, Elson EL. "Effects of cytochalasin D and latrunculin Bon mechanical properties of cells.", J Cell Sci. 114, 1025-1036 (2001 ).
Wang N, Tytell JD, Ingber DE. "Mechanotransduction at a distance: mechanically coupling the extracellular matrix with the nucleus", Nat Rev Mal Cell Biol. 10, 75-82 (2009).
Chalut KJ, Höpfler M, Lautenschläger F, Boyde L, Chan CJ, Ekpenyong A, Martinez-Arias A, Guck J. "Chromatin decondensation and nuclear softening accompany Nanog downregulation in embryonic stem cells", Biophys J. 103, 2060-2070 (2012).
Ballmann, C. et al. "Stimulated Brillouin Scattering Microscopic Imaging," Sci. Rep. 5, 18139 (2015).
Scarcelli, G. & Yun, S. H. Multistage VIPA etalons for high-extinction parallel Brillouin spectroscopy. Opt. Express 19, 10913-10922 (2011).
Traverso, A. J. et al. "Dual Raman-Brillouin microscope for chemical and mechanical characterization and imaging," Anal. Chem. 87, 7519-7523 (2015).
Antonacci, G. et al. "Quantification of plaque stiffness by Brillouin microscopy in experimental thin cap fibroatheroma," J. R. Soc. Interface 12, 20150843 (2015).
Zhang, Jitao et al., "Brillouin flow cytometry for label-free mechanical phenotyping of the nucleus," Lab Chip, vol. 17, No. 4, pp. 663-670 (2017).
Antonacci, Giuseppe et al., "Biomechanics of subcellular structures by non-invasive Brillouin microscopy," Scientific Reports, vol. 6, No. 37217, pp. 1-7 (Nov. 15, 2016).

* cited by examiner

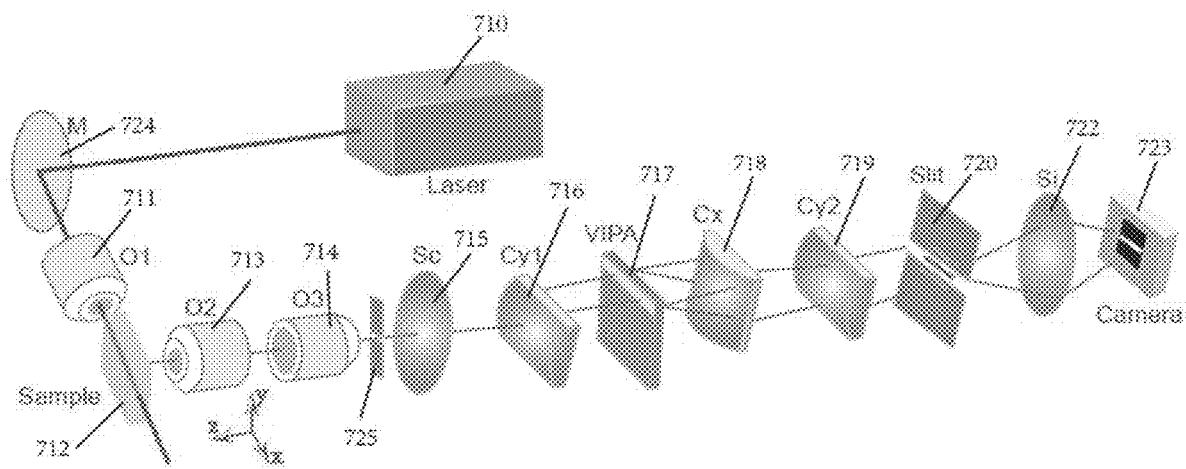
FIG. 7
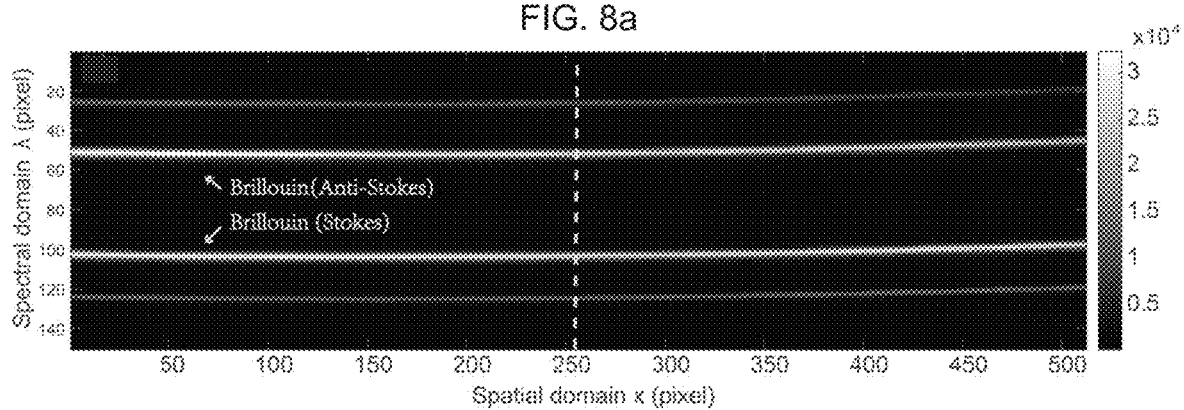
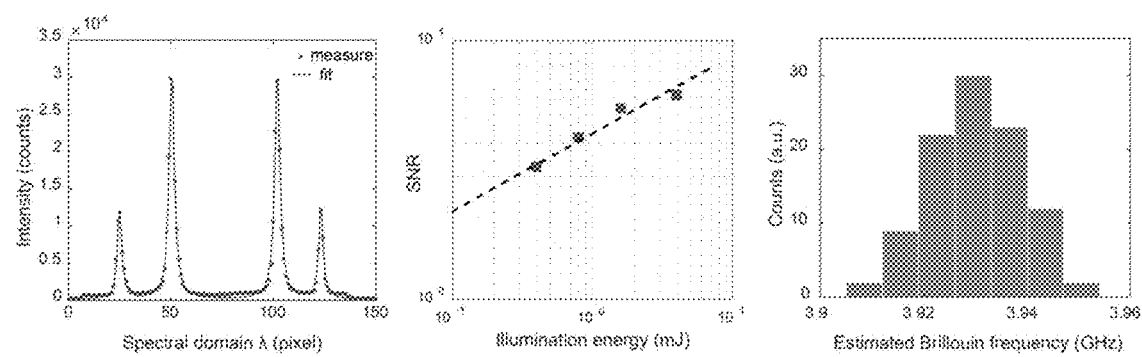
FIG. 8b          FIG. 8c          FIG. 8d

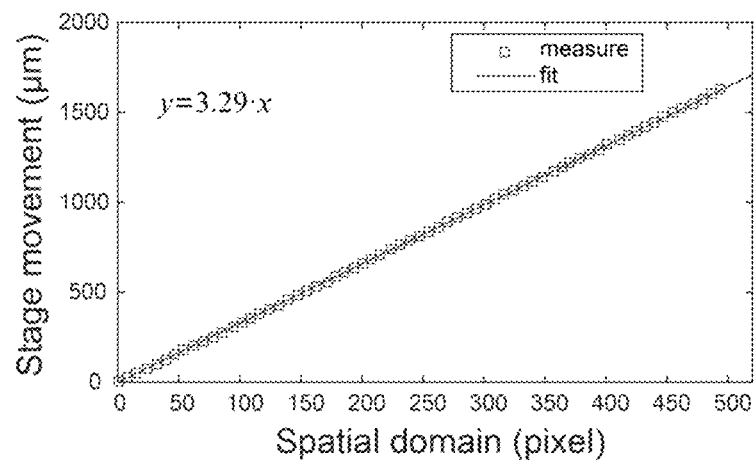
FIG. 9
FIG. 10a
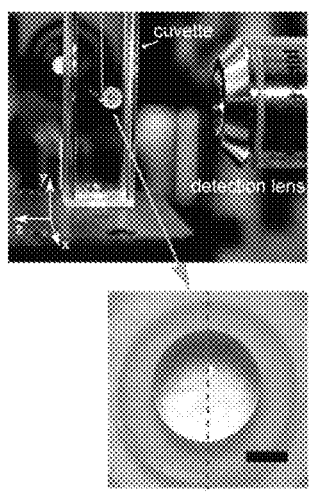
FIG. 10b
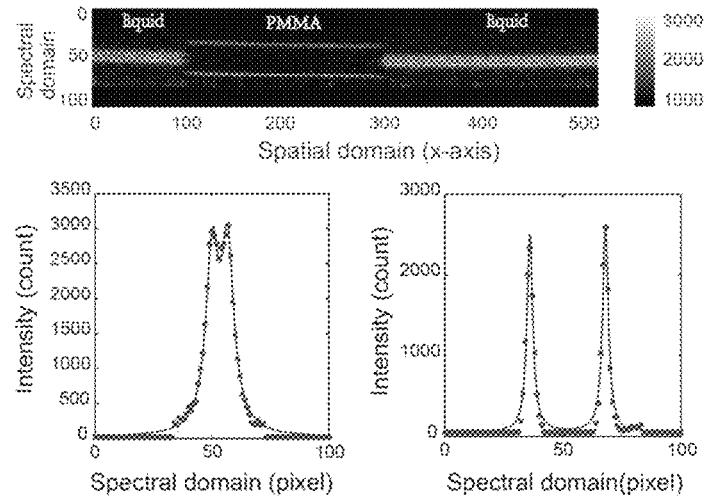
FIG. 10c
FIG. 10d

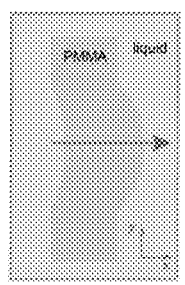 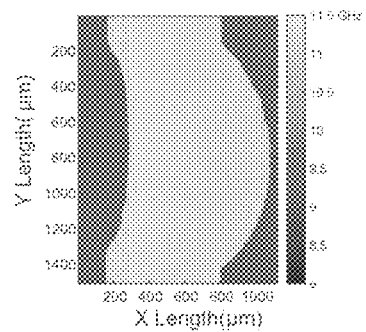 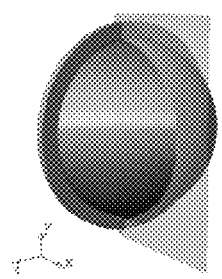
FIG. 11a  FIG. 11b  FIG. 11c
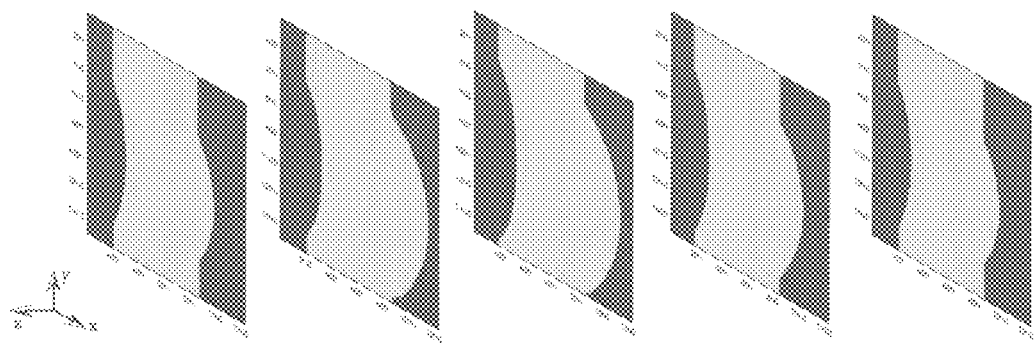
FIG. 11d

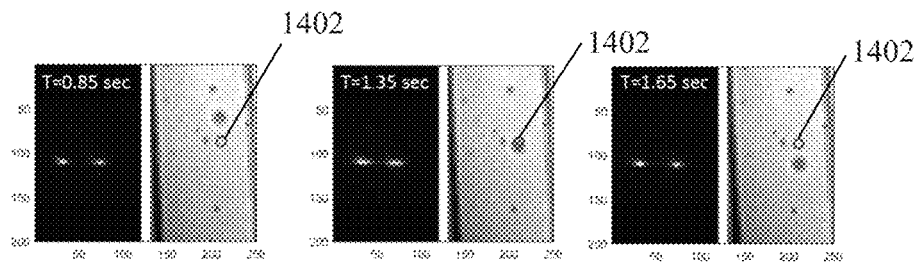
FIG. 14a  FIG. 14b  FIG. 14c
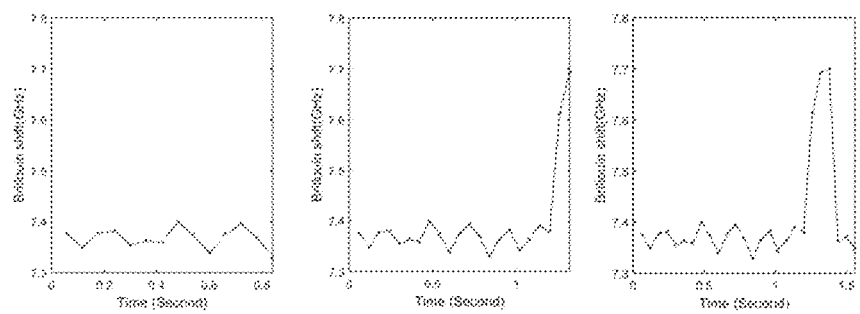
FIG. 14d  FIG. 14e  FIG. 14f
FIG. 15a
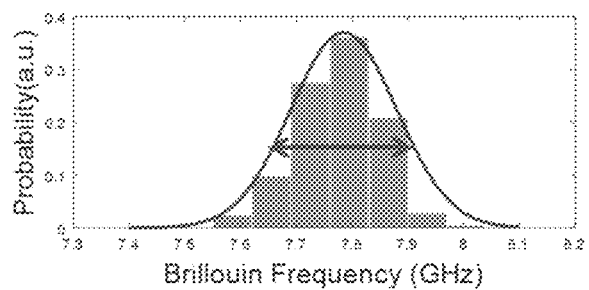
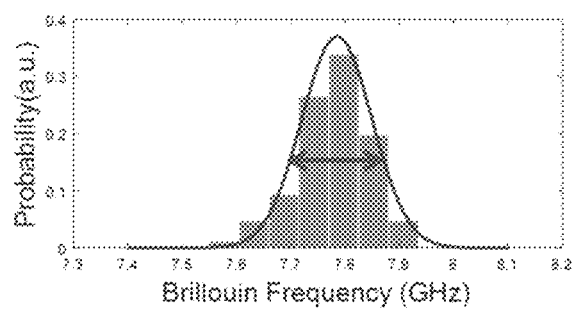
FIG. 15b

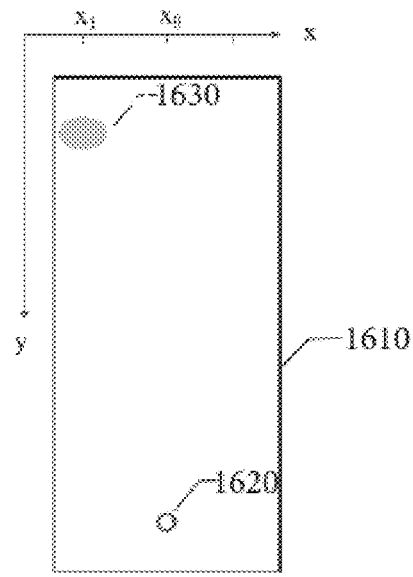
FIG. 16
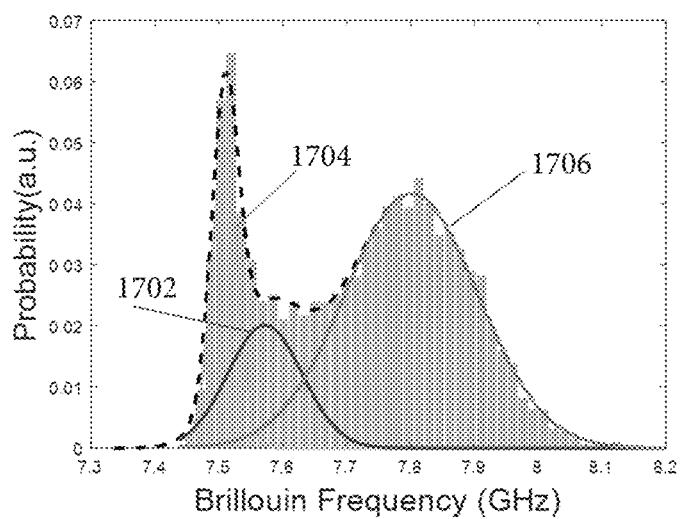
FIG. 17a
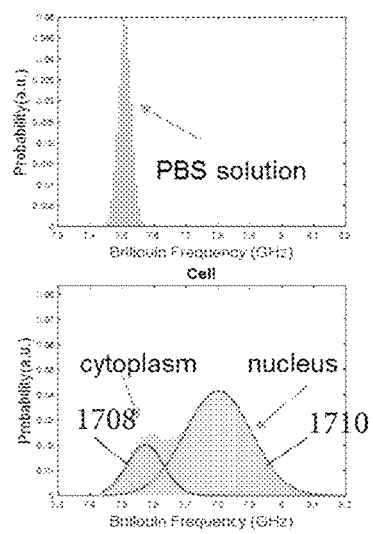
FIG. 17b
FIG. 17c

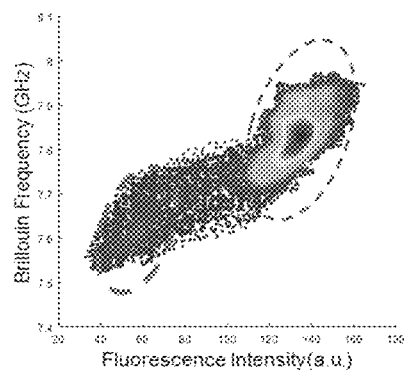 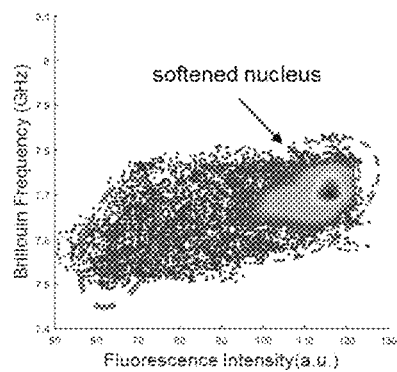
FIG. 23a  FIG. 23b
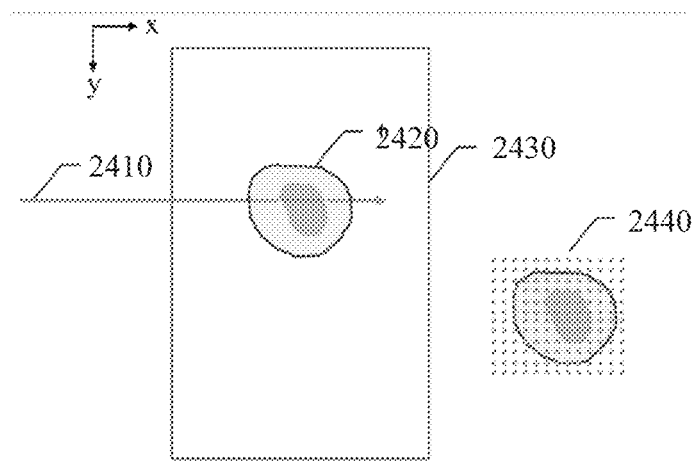
FIG. 24
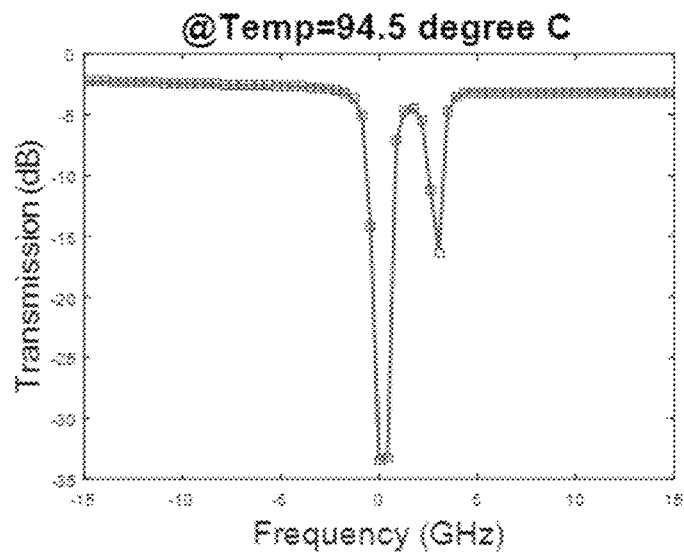
FIG. 25

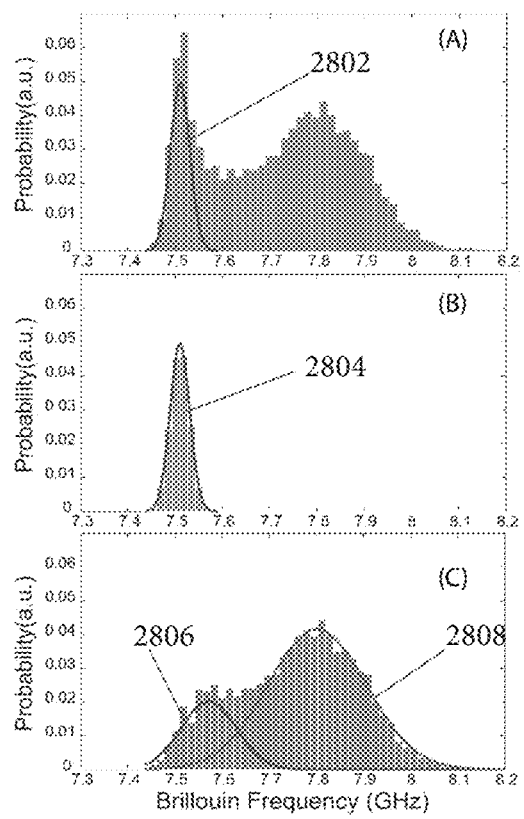
FIG. 28a
FIG. 28b
FIG. 28c
FIG. 29a
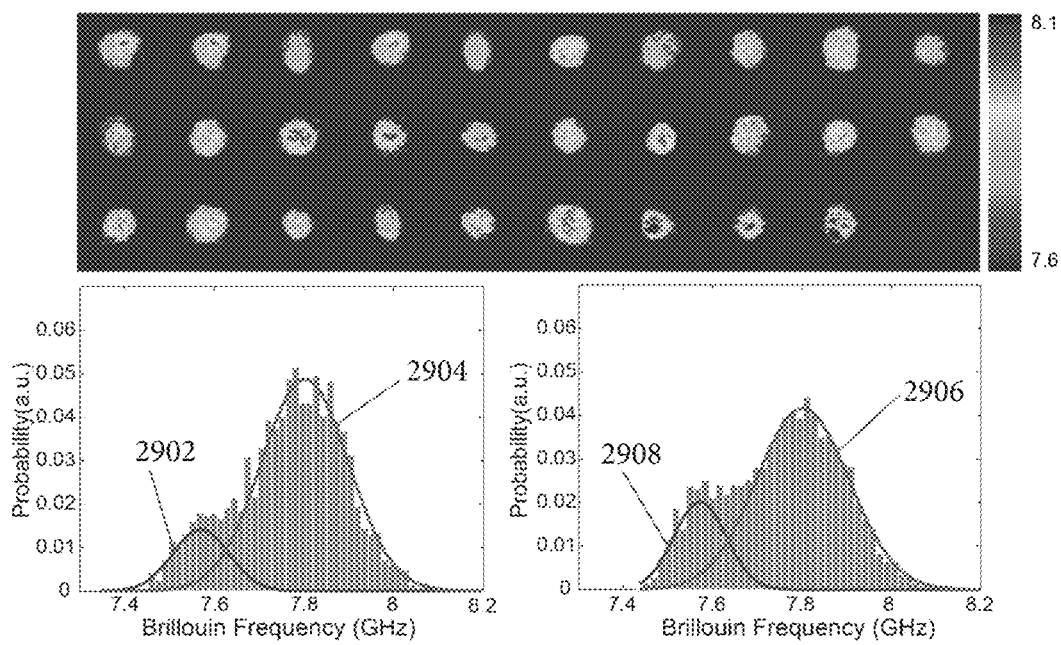
FIG. 29b
FIG. 29c

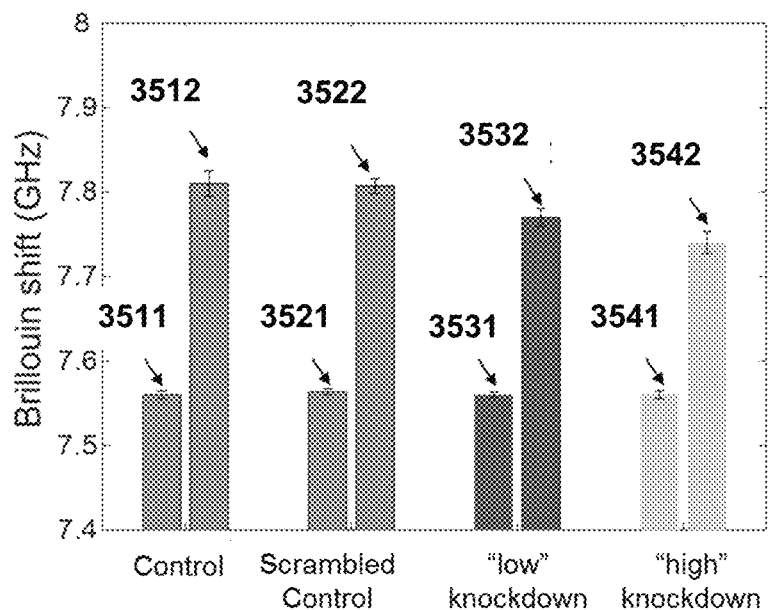
FIG. 35
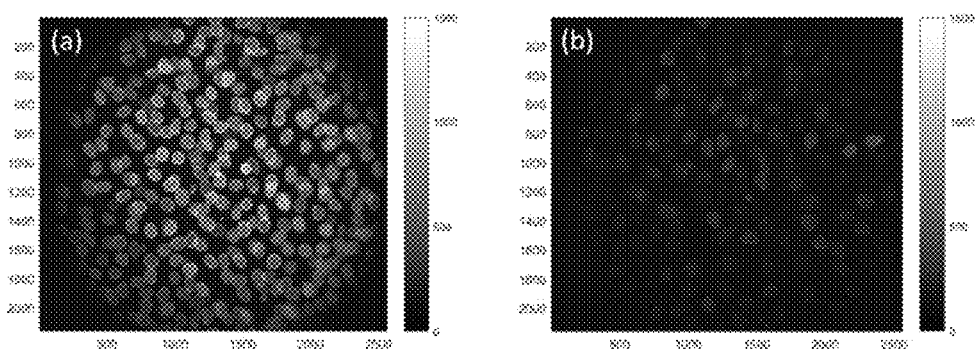
FIG. 36A                    FIG. 36B

CELL CLASSIFICATION BASED ON MECHANICAL SIGNATURE OF NUCLEUS

CROSS-REFERENCE TO RELATED APPLICATIONS

This application is a continuation-in-part of U.S. patent application Ser. No. 15/388,582, filed Dec. 22, 2016, which claims the benefit of U.S. Provisional Patent Application Ser. No. 62/270,982, filed on Dec. 22, 2015; U.S. Provisional Patent Application Ser. No. 62/339,512, filed on May 20, 2016; U.S. Provisional Patent Application Ser. No. 62/323,176, filed on Apr. 15, 2016; and U.S. Provisional Patent Application Ser. No. 62/425,070, filed on Nov. 21, 2016. This application also claims the benefit of U.S. Provisional Patent Application Ser. No. 62/465,230, filed Mar. 1, 2017. All of the above listed applications are incorporated herein by reference in their entirety.

FIELD OF THE INVENTION

The present invention relates to a method and system for classifying cells based on the mechanical signatures of nuclei. Specifically, the method and system according to the present invention are based on the mechanical signatures of cellular nuclei being acquired using label-free cytometry enabled by Brillouin technique. The classification can be accomplished based on either a cell population or a single cell. The present invention additionally relates to methods and systems for identifying cancerous cells in a sample based on the mechanical signatures of the cellular nuclei. Further, the present application provides methods and systems for determining cancel progression based on the mechanical signatures of the cellular nuclei.

BACKGROUND OF THE INVENTION

Cell classification comes from the need to distinguish between different cell types or different phases of the same cell type according to cell characteristics. Distinct features of cellular morphologies and phenotypes are usually used to classify cells, which, however, do not work for cells having similar morphologies or phenotypes. Therefore, various biomarkers have been discovered as complementary approaches for cell classification. Within them, cellular mechanics is a promising biomarker for a large variety of applications.

Cellular mechanics is known to tightly relate to its biological functions and activities, such as proliferation, migration and gene expression (Bao and Suresh, Nature materials 2, 715-725(2003); Vogel and Sheetz, Nat Rev Mol Cell Biol. 7, 265-275 (2006)). For example, when a cell needs to move forward, the contractile force will be generated within the cell body (Stossel, Science 260, 1086-1094(1993)). As a response to the shear flow in the blood vessel, the human endothelial cells will significantly change the expression of shear-stress regulated gene (Mccormick et al., Proc. Natl. Acad. Sci. USA 98, 8955-8960 (2001)). Clinically it shows that highly malignant and metastatic cancer cells are responsible for more than 90% of cancer-related deaths (Wirtz et al., Nat. Rev. Cancer. 11, 512-522 (2011)). In addition to genetic and external environmental factors, biomechanics of the cancer cell is key determinant of its activities. It is consistently found from the various biophysical measurements that cancer cells are softer than normal and benign cells and that this cellular compliance correlates with an increased metastatic potential (Cross et al., Nat. Nanotechnology 2, 780-783 (2007); Guck et al., Biophys J. 88, 3689-3698 (2005)). This correlation is likely from the required optimal mechanical properties of the cancer cell to efficiently migrate through a 3D matrix and/or penetrate through an endothelium during metastasis. It thus strongly indicates that cellular stiffness could be an inherent biomarker to grade the cancer progression. Recently, the nucleus has emerged as a key interest in cell mechanobiology (Dahl et al., Circ. Res. 102, 1307-1318 (2008); Booth et al., Soft Matter 11, 6412-6418(2015); Friedl et al., Curr Opin Cell Biol. 23, 55-64(2011); Denais et al., Science 352, 353-358 (2016); Davidson et al., Cell Mol. Bioeng. 7, 293-306 (2014); Khatau et al., Sci. Rep. 2:488 (2012); Fruleux and Hawkins, J Phys Condens Matter 28, 363002 (2016); Fu et al., Lab Chip 12, 3774-3778 (2012)). Force-induced changes in nuclear shape could result in large-scale reorganization of genetic material within the nucleus (Dahl (2008)). Changes in nuclear stiffness are associated with diseases, such as Huntington-Gilford progeria syndrome (Booth (2015)). As the largest and stiffest organelle within a cell, the nucleus imposes a major physical barrier for cell migration (Friedl (2011)). For cells to migrate through tissue, the nucleus must undergo complex changes in position, shape, and stiffness in coordination with cytoskeletal dynamics (Denais (2016); Davidson (2014); Khatau (2012); Fruleux and Hawkins (2016); Fu (2012)). Thus, nuclear mechanical properties are of great interest because they are closely related to cellular functions and could provide useful biophysical signatures to classify cells.

In the past two decades, many efforts have been made to develop methods to probe mechanical properties (e.g., elasticity and viscosity) of cells, such as micropipette aspiration (Mitchison and Swann, J. exp. Biol. 31, 443-460 (1954)), optical tweezer (Tan et al., J Biomech Eng. 132, 044504 (2010)), optical stretcher (Guck et al., Biophys J. 88, 3689-3698 (2005); Guck et al., Biophys J. 81, 767-784 (2001)), deformability cytometry (Otto et al., Nat Methods 12, 199-202 (2015)), atomic force microscopy (AFM) (Lulevich et al., V Proc Natl Acad Sci USA 107, 13872-13877(2010)), magnetic twisting cytometry (Wang et al., Science 260, 1124-1127 (1993)), and micro-rheology (Weihs et al., Biophys J. 91, 4296-4305 (2006)). However, most of existing methods only provide an average measurement of the mechanical properties of the whole cell and cannot directly assess nucleus. Currently, extracting mechanical properties of the nucleus required staining, along with additional information and assumptions about how forces are transmitted within a cell. For pristine mechanical information, the nucleus has to be isolated to allow AFM or micropipette measurement (Lammerding, Compr. Physiol. 1, 783-807 (2011)), which is not only invasive but also may bias the measurement because of the isolation of the nucleus from the natural environment.

Brillouin scattering is the phenomena of inelastic light scattering induced by acoustic phonon of a material. In order to separate the small (typically in the order of GHz) Brillouin frequency shift from elastically scattered light, high-resolution spectrometer such as a multi-pass scanning Fabry-Perot interferometer is usually used in conventional Brillouin spectroscopy (Lindsay S M, Burgess S and Shepherd I W, "Correction of Brillouin linewidths measured by multipass Fabry-Perot spectroscopy," Appl. Opt. 16(5), 1404-1407 (1977)). Since the dynamics of acoustic phonon is directly linked to the viscoelastic properties of a material, mechanical information can be acquired by measuring the Brillouin frequency shift of the scattered light (Dil J G, "Brillouin scattering in condensed matter," Rep. Prog. Phys.

45, 286-334 (1982)). However, this method is fairly slow due to the point-by-point scan of the spectrum. In addition, the throughput efficiency is limited to the finesse of the etalon. This bottleneck was overcome by using a virtually imaged phased array (VIPA) etalon that can generate large angular dispersion (Xiao S, Weiner A M and Lin C, "A Dispersion Law for Virtually Imaged Phased-Array Spectral Dispersers Based on Paraxial Wave Theory," IEEE J. Quantum Electronics 40(4), 420-426 (2004)) and enables measuring all of the spectral components simultaneously by a CCD camera with high throughput. Using this type of spectrometer, laser-scanning confocal Brillouin microscopy in biological tissue was performed at low illumination power and integration time, where each point in the sample is illuminated sequentially. The Brillouin spectrum was analyzed to create Brillouin-based elasticity maps (Scarcelli G and Yun S H, "Confocal Brillouin microscopy for three-dimensional mechanical imaging," Nature Photonics 2, 39-43 (2007); Girard M J A, Dupps W J, Baskaran M, Scarcelli G, Yun S H, Quigley H A, Sigal I A and Strouthidis N G, "Translating Ocular Biomechanics into Clinical Practice: Current State and Future Prospects," Curr. Eye Res. 40(1), 1-18 (2015)).

Brillouin spectroscopy allows non-invasive measurement of mechanical properties by measuring the frequency spectrum of acoustically-induced light scattering within a sample. Brillouin microscopy at sub-micron resolutions enabled the measurement of cell physico-chemical properties (Scarcelli G, Polacheck W J, Nia H T, Patel K, Grodzinsky A J, Kamm R D, Yun S H, "Noncontact three-dimensional mapping of intracellular hydromechanical properties by Brillouin microscopy", Nat Methods. 12, 1132-1134 (2015)). In fact, cell mechanical properties critically regulate many cellular functions, e.g. proliferation, migration, gene expression as well as system-level behaviors, e.g. tissue morphogenesis, metastasis, and angiogenesis. As a result, "mechanical phenotyping", i.e. the ability to classify cells based on their mechanical properties, has emerged as a powerful approach to characterize cell state and physiological/pathological conditions. For example, decreased cell stiffness has been shown to correlate with increased metastatic potential and thus it has been suggested as a novel label-free marker for tumor detection and staging (Swaminathan, V., et al. Mechanical Stiffness Grades Metastatic Potential in Patient Tumor Cells and in Cancer Cell Lines, Cancer Research 71, 5075-5080 (2011); Cross, S. E., Jin, Y. S., Rao, J. & Gimzewski, J. K. Nanomechanical analysis of cells from cancer patients. Nature Nanotechnology 2, 780-783 (2007)).

In related applications a system and method of label-free cytometry based on Brillouin light scattering has been provided which has successfully demonstrated its capability to directly probe the mechanical properties of the nucleus with submicron resolution (Zhang et al., Lab Chip 17, 663-670 (2017)). This method uses a light beam to sense the mechanical information of the sample by measuring the Brillouin frequency shift of the scattered light, and thus is intrinsically non-contact, non-invasive and label-free (Dil, Rep. Prog. Phys. 45, 286-334 (1982); Scarcelli and Yun, Nature Photonics 2, 39-43 (2007); Scarcelli et al., Nat Methods. 12, 1132-1134 (2015)).

SUMMARY OF THE INVENTION

The present invention relates to a method and system for identifying mechanical properties of a cell nucleus through a label-free cell analysis based on Brillouin light scattering techniques. The present application additionally provides a method and system for identifying cancerous cells based on mechanical properties of the cell nucleus.

In one aspect of the invention, a method is provided to simultaneously obtain one or more Brillouin metrics associated with a Brillouin scattering spectrum at multiple points within a sample, wherein at least one point is within the nucleus of the cell. Specifically, the sample is illuminated by a light beam along a first direction. A Brillouin scattered light emitted from the sample in response to the illuminating light beam is collected and sent to an optical arrangement to induce a spectral dispersion and subsequently to a detection unit. The optical arrangement and the detection unit are positioned along a second direction, different from the first direction. A spatio-spectral pattern of the Brillouin scattered light is detected onto the detection unit such that multiple points of the sample along the illuminating light beam are measured simultaneously. Next, the spatio-spectral pattern is calibrated at each spatial point at the detection unit. One or more Brillouin metrics are calculated in the final step at each measured sample point based on the detected spatio-spectral pattern. In one embodiment, the Brillouin metrics provide information regarding at least one mechanical property of the nucleus.

In yet another aspect of the invention, a system is provided to simultaneously obtain one or more Brillouin metrics associated with a Brillouin scattering spectrum at multiple points within a sample, wherein at least one point is within a cell nucleus. Specifically, the sample is illuminated by a light beam provided by a light source along a first direction. One or more lenses collect a Brillouin scattered light emitted from the sample in response to the illuminating light beam and guide the Brillouin scatted light to an optical arrangement to induce a spectral dispersion and subsequently to a detection unit. The optical arrangement, the one or more lenses, and the detection unit are positioned along a second direction, different from the first direction. A spatio-spectral pattern of the Brillouin scattered light is detected onto the detection unit such that multiple points of the sample along the illuminating light beam are measured simultaneously. A processor in communication with the detection unit calibrates the spatio-spectral pattern at each spatial point to account for the angular dispersion at the VIPA. Furthermore, the processor calculates one or more Brillouin metrics at each measured sample point based on the detected spatio-spectral pattern. In one embodiment, Brillouin metrics are selected from the group consisting of: Brillouin frequency shift, Brillouin spectrum line width, Brillouin gain or loss spectrum, and a combination thereof. In yet another embodiment, the physical properties of the sample are selected from the group consisting of: viscoelastic modulus, density, refractive index, electrostriction, and a combination thereof.

In yet another aspect of the invention, a method and system for classifying biological cells is provided. The system includes a container having a biological sample including the biological cells in a media. Next, the biological sample is illuminated by a light source to generate a Brillouin scattered light from within the biological cells and the media. A processor calculates a Brillouin scattering spectrum at multiple points within each biological cell. One or more Brillouin metrics related to subcellular physical properties at different spatial points within the biological cells are calculated by the processor based on the measured Brillouin scattering spectrum. Furthermore, the processor classifies the biological cells based on physical properties at different spatial points within the biological cells. In one embodiment, the metric related to subcellular physical properties is a Brillouin frequency shift. The processor is further configured to generate a histogram for the Brillouin frequency shift including each measured point within the biological cells. A linear superposition of Gaussian distributions is applied by the processor to fit the histogram. Next, the processor determines each peak within the histogram, wherein the peaks represent mechanical signatures from different regions within the cells. The physical properties at different spatial points within the biological cells are correlated to the determined mechanical signatures.

In yet another aspect of the invention, the mechanical properties of the nucleus can be used to identify cells that are cancerous within the sample.

BRIEF DESCRIPTION OF THE DRAWINGS

The accompanying drawings, which are incorporated herein and form part of the specification, illustrate various embodiments of the subject matter of this disclosure. In the drawings, like reference numbers indicate identical or functionally similar elements.

FIGS. 4a-4e demonstrate raw images of spectral patterns obtained by using the setup of FIG. 2.

FIG. 7 illustrates a Brillouin spectroscopy setup for the multiplexed scanning mode according to one embodiment of the present invention.

FIGS. 8a-8d demonstrate characterization of the accuracy of the estimated Brillouin frequency shift at a single pixel in spatial domain obtained by using the setup of FIG. 7.

FIG. 8a demonstrates an original dispersion pattern captured by a camera.

FIG. 8b demonstrates a spectral pattern at a single point.

FIG. 8c demonstrates a logarithmic plot of the SNR versus the illumination energy.

FIG. 8d demonstrates a distribution of estimated Brillouin frequencies of the time-trace data.

FIG. 9 demonstrates characterization of the spatial resolution for the measurements obtained according to FIG. 7. The squares represent measured data and the red line represents linearly fitted data.

FIG. 10a demonstrates a picture of a Poly methyl methacrylate (PMMA) lens in a cuvette. The picture was taken before filling the cuvette with an index-matching liquid.

FIG. 10b demonstrates a snapshot of a Brillouin spectral pattern acquired by the camera.

FIG. 10c demonstrates Brillouin spectrum of the index-matching liquid. The dots and solid curves represent measured data and fitted data, respectively.

FIG. 10d demonstrates a Brillouin spectrum of the PMMA lens.

FIGS. 11a-11d demonstrate 2D and 3D Brillouin images of the PMMA lens.

FIG. 11a demonstrates a cross-section of the PMMA lens that was scanned by the setup according to FIG. 7.

FIG. 11b demonstrates a cross-sectional Brillouin image of the PMMA lens at the location indicated by the dotted line in FIG. 10a.

FIG. 11c demonstrates a schematic of the 3D scanning of the PMMA lens.

FIG. 11d demonstrates a 3D Brillouin imaging of the PMMA lens. Each slice represents a cross-section image of the PMMA lens at a location along z-axis.

FIGS. 14a-14c demonstrate snapshots of both the Brillouin signal and bright-field image at different times.

FIGS. 14d-14f are time traces of the Brillouin frequency calculated from the raw Brillouin signal of FIGS. 14a-14c.

FIGS. 15a-15b illustrate the effect of sheath flow on the Brillouin frequency.

FIG. 16 illustrates a principle of aligning a flowing cell to a focused spot of a laser beam according to the current invention.

FIGS. 17a-17c illustrate a cell spectral analysis implemented by using the Brillouin spectroscopy setup according to FIG. 12.

FIGS. 23a and 23b illustrate the effect of Cytochalasyn D on the nucleus obtained by the Brillouin spectroscopy setup of FIG. 21.

FIG. 24 illustrates a conceptual sketch of acquiring a 2D image by using the Brillouin spectroscopy setup of FIG. 7.

FIG. 25 demonstrates a measured absorption spectrum of a gas chamber containing Rubidium gas.

FIG. 28a demonstrates original data containing signatures of both the Phosphate-Buffered Saline (PBS) and the cell. FIG. 28b demonstrates the signature of the PBS itself.

FIG. 28c demonstrates a signature of the cell.

FIG. 29a demonstrates 2D images of a cell population (29 cells).

FIGS. 29b and 29c show a distribution of data points from the 2D images and the flow experiment based on obtaining Brillouin frequencies at multiple points within the cells, respectively.

FIG. 35 illustrates the exemplary results of the third embodiment of this invention. While cytoplasmic properties are unchanged, the nucleus is significantly less stiff in the lamin A/C knockdown sample.

FIGS. 36A-36B illustrates exemplary result of fluorescent images taken using identical parameters. It shows that lamin A/C expression is much lower in the knockdown sample.

DETAILED DESCRIPTION

The present invention has several embodiments and relies on patents, patent applications, and other references for details known in the art. Therefore, when a patent, patent application, or other reference is cited or repeated herein, it should be understood that it is incorporated by reference in its entirety for all purposes as well as for the proposition that is recited.

The present invention relates to a method and system of label-free cell analysis based on Brillouin spectroscopy. Brillouin scattered light emitted from a cell sample allows one to obtain physical information characterizing the sample. In one aspect of the invention, to achieve this, the sample is illuminated by a light beam along a first direction, and the emitted by the sample Brillouin scattered light is collected and detected along a second direction. Multiple positions of the sample along the first direction can be measured simultaneously thereby effectively improving the measurement throughput. Furthermore, biological cells in a sample can be classified based on subcellular information obtained from the Brillouin spectrum.

The Brillouin frequency shift $f_b$ of an isotropic material can be expressed as $$f_b = \frac{2n}{\lambda} \cdot V \cdot \cos(\theta/2) \qquad (1)$$

where n is the refractive index of the material, $\lambda$ is the wavelength of the laser, $V=\sqrt{E/\rho}$ is the acoustic velocity, E is the elastic modulus and $\rho$ is the density, B is the scattering angle (here $\theta=90°$).

By measuring one or more metrics associated with a Brillouin scattering spectrum at multiple points within a sample, direct readout of mechanical and/or physical properties of the measured sample can be achieved. In one embodiment, Brillouin frequency shift is used as a metric. The mechanical and/or physical properties of a sample may include viscoelastic modulus, density, refractive index, and electrostriction. Other metrics such as Brillouin spectrum line width, Brillouin gain or loss spectrum, and a combination thereof can be used for determining mechanical and/or physical properties of the measured sample.

Figure 1:
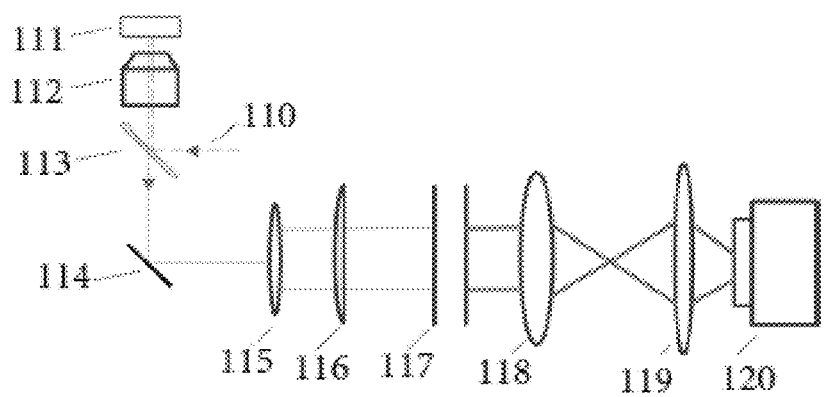
FIG. 1 illustrates a Brillouin spectroscopy setup for the point-by-point scanning mode.

FIG. 1 demonstrates a Brillouin spectroscopy setup for a point-by-point scanning mode using epi-detection with a microfluidic channel 111. Specifically, an incoming laser beam 110 is first guided by a beam splitter 113 and then focused onto the microfluidic channel 111 by an objective lens 112. The excited Brillouin scattering light is collected by the same objective lens 112 and guided to a collimator 115 by the beam splitter 113 and a mirror 114. The collimated beam after the collimator 115 is first focused by a cylindrical lens 116 and then sent into a VIPA 117. Different spectral components of incoming scattering light are separated in space by the VIPA 117 and focused by a spherical lens 118 to generate a spectral pattern. The spectral pattern is then imaged by a spherical lens 119 onto a detection unit 120. By way of example, the detection unit 120 may be a camera. In some embodiments, the spherical lens 119 may be not necessary and as such the camera 120 can be placed directly at the front focal plane of the spherical lens 118. When a sample is flowed through the microfluidic channel 111, its Brillouin signature can be identified and correlated to its intrinsic physical properties. Accordingly, as only one point at the focal plane of the objective lens 112 can be measured each time, point-by-point scanning is needed for imaging purpose.

Figure 2:
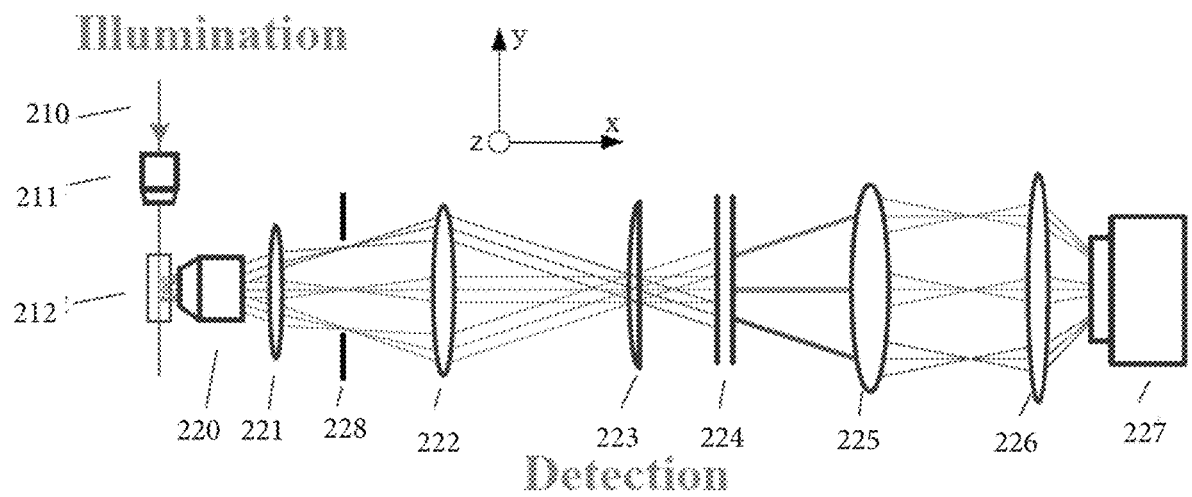
FIG. 2 illustrates a Brillouin spectroscopy setup for the multiplexed scanning mode according to one embodiment of the current invention.

FIG. 2 relates to one embodiment of the current invention using multiplexed Brillouin spectroscopy in conjunction with a microfluidic chip. Specifically, an incoming illumination light beam 210 is reshaped by an objective lens 211 to generate a pencil beam within a microfluidic chip 212 having a sample. The detection path (along x-direction) leading to a detection unit 227 is orthogonal to the illumination path (along y-direction). By way of example, the detection unit 227 may be a camera. The scattering light generated within the chip 212 is first collected by a second objective lens 220 and an intermediate image is generated at the focal plane of a tube lens 221. In one embodiment, a spatial filter or aperture 228 is positioned in an intermediate image plane to reject out-of-focus light coming from the sample. A spherical lens 222 is placed such that the intermediate image is on its back focal plane, thus the light is collimated by the spherical lens 222. The collimated light is then focused by a cylindrical lens 223 in z-direction onto a VIPA 224. Different spectral components of incoming scattering light are separated in space by the VIPA 224 and focused by spherical lens 225 to generate spectral pattern. The spectral pattern is then imaged by spherical lens 226 onto a camera 227. In the detection path, three groups of beam lines with indicate different positions of the sample. It can be seen in FIG. 2, that within the field of view of the objective lens 220, multiple position of the sample can be measured in parallel. In some embodiments, the spherical lens 226 may be omitted such that the camera 227 is placed directly at the front focal plane of the spherical lens 225.

Since the collected scattering light from all of the measured positions along the illumination beam is collimated by the same spherical lens 222, the collimated beam from different position has different angle in xy-plane for the VIPA 224. This will result in an additional spatial shift of the spectra for the off-axis points with regard to the on-axis point, and thus the spectra along spatial dimension (i.e. y-direction) are not straight but curved on the camera 227. Accordingly, the incident angles of the scattering light from different points across the illumination line are different. This means that the scattering from different points in the sample will have slightly different path-length and dispersion within the VIPA etalon. To eliminate the angular dispersion and hence the bending of spectral lines, the imaging magnification that occurs at the intermediate imaging plane of the lens 221 was minimized. After the spectral dispersion has occurred at the VIPA 224, the imaging magnification can be restored without affecting the curvature of spectral lines on the camera 227.

Furthermore, to compensate for the angular dispersion, the spectral calibration may be required. When the illumination beam line is present in the spectrum detected on the camera 227, the spectral calibration can be performed at each pixel of the spatial line (corresponding to one point of the sample) using the location of the unshifted illuminating beam line at the various diffraction orders of the VIPA etalon. When the illuminating beam lines are not available, there are two unknown parameters that are needed for calibration at each spatial point: free spectral range (FSR) and spectral dispersion factor. Therefore, a combination of results of two or more known samples is sufficient to solve for the unknown parameters.

Figure 3:
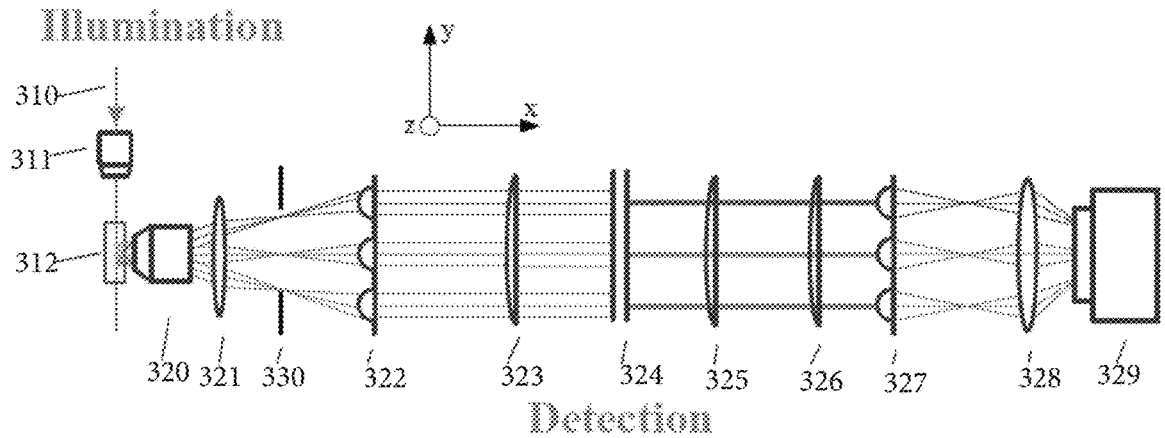
FIG. 3 illustrates a Brillouin spectroscopy setup for the multiplexed scanning mode according to another embodiment of the current invention.

Alternatively, the spatial calibration can be avoided by using another embodiment of the current invention based on the multiplexed Brillouin spectroscopy as demonstrated in FIG. 3.

FIG. 3 illustrates a multiplexed Brillouin spectroscopy setup using a lens array according to another embodiment of the present invention. The illuminating path is the same as that in FIG. 2. A microfluidic chip 312 is illuminated by the reshaped beam of the light 310 using the objective lens 311. The detection path (along x-direction) is in the normal direction of the illumination path (along y-direction). The scattering light generated within the chip 312 is first collected by a second objective lens 320. An intermediate image is generated at the focal plane of the tube lens 321. In one embodiment, a spatial filter or aperture 330 is positioned in an intermediate image plane to reject out-of-focus light coming from the sample. The spherical lens 222 of FIG. 2 is replaced by a lens array 322 for collimation purpose. Each lenslet of the lens array 322 only accepts light from small portion of the intermediate image so that the entire image is divided into many sections and each is collimated by a lenslet independently. Because each small section is approximated as on-axis for a lenslet and all of the lenslets are well aligned, the overall collimated beam is parallel and the corresponding spectra will be straight. The collimated light is then sent into a VIPA 224. A pair of cylindrical lenses 325 and 326 is used to compress the output light of the VIPA 224 in order to fit the aperture of the lenslet of a second lens array 327. The spectral pattern is generated at the front focal plane of the lens array 327 and imaged onto the detection unit 329 by a spherical lens 328. By way of example, the detection unit 329 may be a camera. In some embodiments, the spherical lens 328 may be omitted, such that a camera 329 can be placed directly at the front focal plane of the lens array 327.

Example 1

Figure 4F:
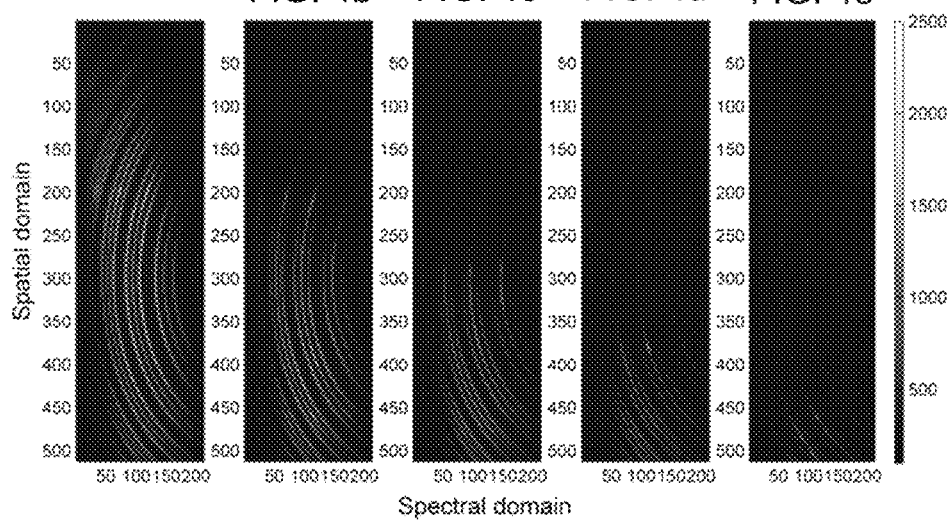
FIG. 4f demonstrates characterization of the spatial resolution for measurements associated with FIGS. 4a-4e. The squares represent measured data and the blue line represents linearly fitted data.
Figure 4F:
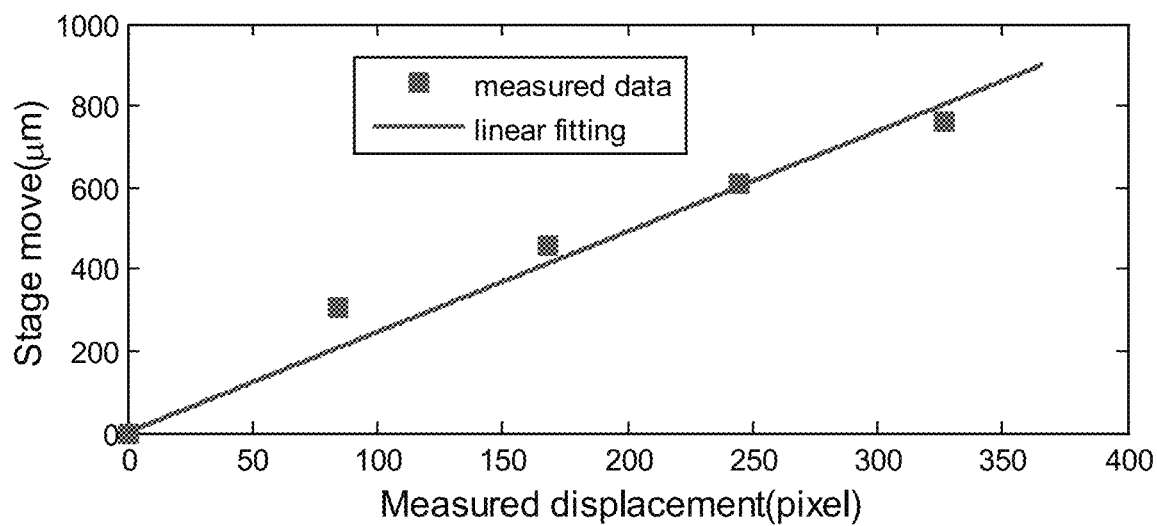

As an example of validation of the current invention, an experiment was implemented to demonstrate the spatial resolution of the multiplexed Brillouin spectroscopy using the setup of FIG. 2 In this experiment, a single-mode 532 nm continuous-wave laser was used as a light source, a plastic cuvette containing methanol was used as a sample. The objective lens 211 in the illumination path (along y-axis) has a numerical aperture (NA) of 0.0175, and the objective lens 220 in the detection path (along x-axis) has a NA of 0.1. The VIPA 224 has a free spectral range (FSR) of 17 GHz and entrance window of 20 mm. The camera 227 is an electron multiplying coupled charge device (EMCCD). A knife edge was placed between the sample (the plastic cuvette) and the objective lens 220. The knife edge can be moved along y-direction using a translational stage. When moving the knife edge towards y-direction, the scattering signal from the cuvette will be partly blocked. By comparing the displacement of the knife edge and the recorded signal of the camera, the spatial resolution of the spectroscopy can be acquired. FIGS. 4a-4e show the raw images captured by the camera when the knife edge was at different position. In these images, multiple spectral orders in spectral domain were shown. Each order contains a group of three fringes, with two Brillouin frequencies (Stokes and anti-Stokes shift) at both sides and laser frequency in between. FIG. 4f shows a linear relationship between the knife edge's movement and measured displacement. It indicated that one pixel of the camera is corresponding to a size of 2.45 µm of the sample. It also indicates that the current setup as shown in FIG. 2 can measure as large as 800 µm of the sample, so that more than 300 points can be measured simultaneously.

Figure 5:
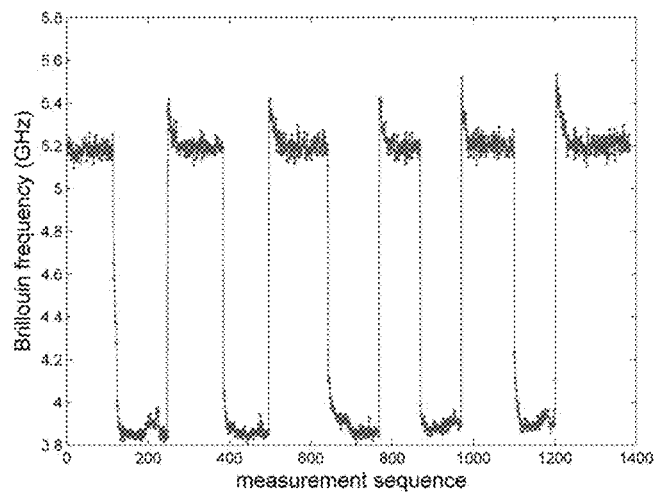
FIG. 5 demonstrates the Brillouin frequency associated with two different liquids flowing through a microfluidic channel.

The measurement of flowing liquid in a microfluidic channel using the embodiment of the current invention as shown in FIG. 2 was demonstrated in FIG. 5. A microfluidic channel made of fused silica glass has a width of 100 µm and a depth of 250 µm. The channel layer was sandwiched by two glass windows with a width of 500 µm. The channel located in the middle of a 1-inch by 2-inch chip, whose sides were polished to allow light beam to pass through. During measurement, the chip was up-straight placed so that the liquid can flow in the channel along z-direction. The laser beam 210 illuminates the channel from the side of the chip. Water (with Brillouin frequency shift of 5.2 GHz) and methanol (with Brillouin frequency shift of 3.9 GHz) were pumped alternately into the channel through tubing by handheld syringes. The integration time of the camera was 0.2 second, which is also the time period of the measurement sequence. FIG. 5 indicates that the flowing liquid in the microfluidic channel can be clearly identified by the multiplexed Brillouin spectroscopy. This experiment demonstrates the capability of the current invention in the application of flow cytometry.

Figure 6:
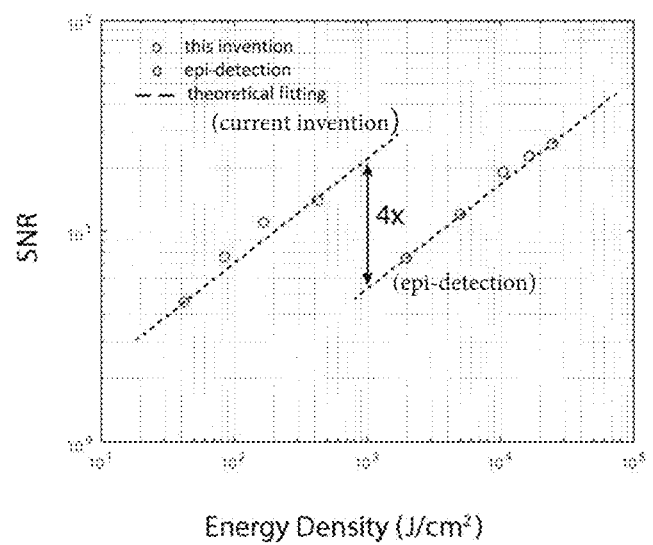
FIG. 6 illustrates a signal-to-noise ratio (SNR) comparison between the multiplexed Brillouin spectroscopy according to the present invention and conventional point-by-point Brillouin spectroscopy.

As another evidence of the advantage of the current invention according to the embodiment demonstrated in FIG. 2, the signal-to-noise ratio (SNR) between the current invention (FIG. 2) and conventional epi-detection setup (FIG. 1) was compared. The SNR of each setup was measured at different input power density of the light and exposure time of the camera. FIG. 6 indicates that this invention is shot-noise limited (theoretical fitting) and has much higher SNR than conventional epi-detection at the same input energy density. In other words, this invention enables faster measurement than conventional epi-detection at the same SNR level.

Beyond the method described above, there are other ways to further improve the measurement throughput. In one embodiment, one can place a transducer underneath the microfluidic channel as an exciting source to enhance the acoustic signal generated by the sample. In addition, stimulated Brillouin scattering is usually much stronger than spontaneous Brillouin scattering. Instead of using single-wavelength light source, one can use two lasers with tunable wavelength to generate stimulated Brillouin scattering within the microfluidic channel to further enhance the signal. Moreover, one can also use one ultrashort pulsed laser to generate impulsive stimulated Brillouin scattering.

Example 2

Example 2 relates to characterization of the multiplexed (line-scanned) Brillouin spectroscopy according to the embodiment of the current invention as shown in FIG. 7. FIG. 7 demonstrates a line-scanned Brillouin spectroscopy setup including a mirror 724, objective lenses 711, 713, and 714, a spherical lens 715 for beam collimation, cylindrical lenses 716, 718, and 719, and a spherical lens 722 for imaging purpose. In one embodiment, a spatial filter or aperture 725 is positioned in an intermediate image plane to reject out-of-focus light coming from the sample.

The spectral resolution of the spectrometer according to FIG. 7 was characterized in the current example. In one non-limiting embodiment, the light source 710 was a single mode 532-nm cw (continuous-wave) laser (Torus, Laser-Quantum). The light from the laser head was focused by the objective lens 711 (NA=0.0175) to generate a line beam for illuminating the sample 712. At 90 degree, the scattering light along the beamline was first imaged by a pair of objective lens 713 and 714 (both were 4×/0.1NA), and then collimated by a spherical lens 715 (f=400 mm). The collimated light was then focused onto the entrance of a VIPA 717 (FSR=17 GHz, finesse=35) by a cylindrical lens 716 (f=200 mm). The dispersed light after the VIPA 717 was imaged onto the plane of a slit 720 by a pair of cylindrical lens 718 (f=1000 mm) and 719 (f=400 mm). This plane was re-imaged onto the camera 723 (iXon, Andor) by a spherical lens 722 (f=60 mm). By adjusting the aperture of the slit 720, we could block the undesired frequency and only let Brillouin frequency components pass.

A plastic cuvette 712 containing pure methanol is used as a sample. The original dispersion pattern obtained by the camera 723 is shown in FIG. 8a. The two gray lines of the top and bottom are elastic scattering frequency (same as laser's frequency) and the two bright lines in between are Brillouin frequencies (Stokes and Anti-Stokes components). The horizontal axis and vertical axis correspond to spatial and spectral domain, respectively.

FIG. 8b shows the Brillouin spectrum at the location indicated by the dotted line in FIG. 8a. Since the free spectral range of the VIPA was 17 GHz, it could be calculated that the spectral resolution was 0.177 GHz per pixel. The finesse of about 35 was also confirmed by calculating the ratio of the space of successive laser frequency's peak and the full width at half maximum. The accuracy of the estimated Brillouin frequency shift was characterized by calculating the signal-to-noise-ratio (SNR) for each pixel in spatial domain.) FIG. 8c shows a logarithmic plot of the SNR versus illumination energy. The SNRs in FIG. 8c were calculated with different illumination energy. The measured data showed near square-root dependence, indicating shot-noise limited behavior. FIG. 8d shows the representative distribution of the estimated Brillouin frequency at a single point for 100 times measurements, which has a Gaussian shape. The standard deviation of this distribution was used to estimate the accuracy of the estimated Brillouin frequency. In this case it is 8.5 MHz, which corresponds to the relative uncertainty of 0.22%.

In order to characterize the spatial resolution, a knife edge was placed right after the cuvette 712, but before the detection objective lens 713. In one embodiment, a translational stage carrying the knife edge was moved in x-direction with step size of 25.4 μm, and the corresponding image of the knife edge was monitored by the spectrometer's camera 723. The result is shown in FIG. 9. The measured data was linearly fitted, and thus the spatial resolution was calculated as 3.29 μm per pixel. The camera 723 had 512 by 512 pixels in total, which corresponded to nearly 1.68 mm in the sample plane. As shown in FIG. 8a, the spectral lines were not perfectly straight across the spatial dimension but had slight curvature due to the deviation of the incident angles of off-axis points at the VIPA 717. This curvature may result in variation of spectral resolution across the camera; the variation was minimized to less than 0.2 MHz per pixel, i.e. no more than 10 MHz within more than 1-mm spatial field of view. In some embodiments, this error can be avoided by calibration of spectral resolution at each point if necessary.

Example 3

Two-Dimensional and Three-Dimensional Imaging

Example 3 relates to characterization of two-dimensional and three-dimensional imaging based on the multiplexed Brillouin spectroscopy according to FIG. 7.

The Brillouin shift of an aspherical PMMA lens was measured in the setup shown in FIG. 10a. FIG. 10a shows a picture of the PMMA lens taken before filling cuvette with index-matching liquid. The lower is zoomed-in picture of the PMMA lens, the scale bar has a length of 500 μm. The PMMA lens was placed into a plastic cuvette, which was pre-filled with refractive-index-matching liquid to reduce the scattering at the surface of the sample. The cuvette was carried by a vertically placed motorized translation stage, which enabled us to scan the sample in y-direction. In one embodiment, the cuvette (sample 712 in FIG. 7) has a size of 10 mm by 10 mm. To suspend an aspherical Poly methyl methacrylate (PMMA) lens in the central region of the cuvette 712, the margin of the PMMA lens was attached to the tip of a syringe's needle using optical adhesive, and then the end of the needle was fixed to the wall of the cuvette. By way of example and without limitation, the motorized translational stage (T-LSM025A, Zaber) had a 25-mm traveling range and RS-232 control. The maximum speed of the translational stage can be as fast as 7 mm/s.

In one embodiment, a LabView program is used to synchronize the stage movement and camera acquisition so that the scanning could be carried out automatically. The laser power was 70 mW, and the exposure time of the camera was 0.1 second. The speed of the stage was set as 50 μm/sec so that 300 frames were captured within 30 seconds, which corresponded to a displacement of 1.5 mm in total. When the sample (PMMA lens) was immersed into the liquid, it was almost invisible by naked eye because of the refractive index matching. However, since the stiffness of the sample and the matching liquid were different, they could be easily identified by Brillouin spectra. FIG. 10b is a snapshot of the representative signal acquired by the camera 723, in which only Brillouin frequency components were shown because the elastic frequencies were blocked by the slit 720. It is clearly shown in FIG. 10b that the PMMA lens was surrounded by the matching liquid. FIGS. 10c and 10d show the Brillouin spectra of the index-matching liquid and PMMA at a single point, respectively. The dots and solid curves correspond to measured and fitted data, respectively. Using the characterization data of the spectral resolution, the Brillouin frequency shifts of PMMA and the matching liquid were determined as 11.32 GHz and 9.11 GHz, respectively.

FIGS. 11a-11d shows 2D and 3D Brillouin images of the PMMA lens. FIG. 11a indicates the scanned cross-section along the dotted line in FIG. 10a. The arrow indicates an illumination beam. FIG. 11b shows the 2D imaging of the PMMA lens immerged in the matching liquid based on the measured Brillouin frequency shift. In one embodiment, the overall size of the image was around 1.1 mm by 1.5 mm. The interface between the PMMA lens and the matching liquid can be clearly seen from the image, and the inner region of the PMMA lens is pretty uniform. At the interface of different materials, there is cross-talk between two Brillouin signatures corresponding to each material. This cross-talk effect will introduce an ambiguous region at the interface if the two materials have similar Brillouin shift. In this experiment, the PMMA lens and index-matching liquid have distinct Brillouin shift, which allows one to quantify the ambiguous region to be within 2 pixels, i.e. 6.58 μm. It was demonstrated that the capability of this spectrometer to do a rapid 3D imaging by use of the scanning method shown in FIG. 11c. FIG. 11d shows five slices of obtained cross-section images as the PMMA lens is moved along z-axis using another translational stage.

In summary, referring to FIGS. 1-11d, in one embodiment of the current invention, the illuminating beam may be a laser beam and the detection unit 120, 227, 329, and 723 may be a CCD, CMOS camera, or an array of detectors. In yet another embodiment, the illuminating light is provided by an illuminating source having a single wavelength in the UV, visible, or IR regime, either fixed or tunable around its center value. To generate an image of a sample based on the one or more Brillouin metrics calculated at each measured sample point, the sample may be placed on a moving platform to move relative to the illuminating light beam during imaging or acquisition. In yet another embodiment, the illuminating light beam may be moving relative to a static sample during imaging. By way of example and without limitation, the sample may be a biological sample including biological organism, tissue, or biological cells. In one embodiment, the biological cells are living cells. The biological cells may be suspended, adherent to 2D substrates, or cultured within 3D extracellular matrices while measuring Brillouin metrics.

In one embodiment, the spectrum detected on the camera 120, 227, 329, and 723 is a spatio-spectral pattern of the Brillouin scattered light. One or more Brillouin metrics can be calculated at each measured sample point based on the detected spatio-spectral pattern. By way of example and without limitation, a Brillouin metric may be a Brillouin frequency shift, Brillouin spectrum line width, Brillouin gain or loss spectrum, and a combination thereof. Each of the Brillouin metrics measured at a sample point is indicative of physical characteristics of the sample at this point. By way of example and without limitations, physical characteristics of the sample may be viscoelastic modulus, density, refractive index, electrostriction, and combination thereof. In one embodiment, the metric associated with the Brillouin scattered light is a Brillouin frequency shift.

An image of the sample can be generated based on the one or more Brillouin metrics at each measured sample point. Although FIGS. 2, 3, and 7 illustrate illumination and detection path arranged under the angle of 90 degrees, both setups can be implemented with the illumination and detection paths arranged at any angle greater than zero relative to each other.

With the reference to FIGS. 2-3 and 7, an optical arrangement to induce spectral dispersion may comprise spherical lenses, cylindrical lenses, VIPA. Specifically, the optical arrangement comprises elements 222, 223, 224, 225, and 226 of FIG. 2; elements 322, 323, 324, 325, 326, 327, and 328 of FIG. 3; and elements 715, 716, 717, 719, 720, and 722 of FIG. 7. In one embodiment, the optical arrangement inducing a spectral dispersion comprises a virtually imaged phased array (VIPA), a Fabry-Perot etalon, or an echelle grating. In yet another embodiment, the optical arrangement further comprises optical elements to modify size, shape, and/or angular spread of the spatio-spectral pattern in an optical path from the sample to the detection unit. Specifically, the illuminating light beam is reshaped by a first lens 211, 311, and 711 to generate a pencil beam within a container containing the sample. A spatial light modulator or deformable mirror (FIG. 7, mirror 724) may be used to reshape the illuminating light beam entering a first lens (FIG. 7, lens 711). In yet another embodiment, the Brillouin scattered light generated within a sample container is collected by a first imaging system comprising the second lens 220, 320, 713 and generating an intermediate image at a focal plane of a third lens 221, 321, 715. A magnification of the intermediate image is optimized to minimize an angular dispersion of the measured sample points at the VIPA 224, 324, and 717. A spatial filter or aperture 228, 330, and 725 may be used in an intermediate image plane to reject out-of-focus light coming from the sample.

A second imaging system, which is a combination of elements 222, 225, 226 of FIG. 2, elements 322, 326, 327, and 328 of FIG. 3, and elements 715, 718, and 722 of FIG. 7, projects the intermediate image onto the detection unit 227, 329, 723, wherein the optical arrangement, including the VIPA, is in an infinity space of the second imaging system. In a further aspect of the present invention, the Brillouin scattered light is collimated by a spherical lens (FIG. 2, lens 222; FIG. 7, lens 715) and focused by a cylindrical lens (FIG. 2, lens 223; FIG. 7, lens 716) in z-direction onto the VIPA, wherein collimated beams from different positions have different angle in xy-plane for the VIPA. The output light of the VIPA is modified by several cylindrical and spherical lenses 225, 226, 718, 719, 722 to place the Brillouin spatio-spectral pattern in sharp focus onto the detection unit 227, 329, 723. Yet, in another aspect of the invention, the Brillouin scattered light is collimated by a first lens array 322, wherein each lenslet of the first lens array only accepts light from a portion of the intermediate image, wherein the entire image is divided into multiple sections, each section collimated by a lenslet independently. The output light of the VIPA is compensated by a pair of cylindrical lens 325 and 326 to fit an aperture of a lenslet of a second lens array 327. The Brillouin spatio-spectral pattern is generated at a front focal plane of the second lens array 327 and imaged onto the detection unit 329.

In yet another embodiment, a narrowband filter to absorb the laser line in the spatio-spectral pattern, the narrowband filter selected from the group consisting of: an absorption gas cell and a Fabry-Perot etalon device. The wavelength of the illuminating source and the wavelength absorbed by the narrowband filter are locked to each other.

In one embodiment, the Brillouin spatio-spectral pattern is calibrated by measuring on the detection unit 227, 329, 723 a distance between different laser or elastic scattering lines generated by different orders of diffraction of the optical arrangement. In yet another embodiment, when the laser line is absorbed by the narrowband filter and not available for calibration, reference materials of known Brillouin properties are used to calculate the spectral dispersion properties of the optical arrangement.

To understand advantages and limitations of the setup as demonstrated in FIG. 7, the spectral efficiency of angled geometries were compared with traditional setups using confocal epi-detection configuration as demonstrated in FIG. 1. If the illumination beam is vertically polarized and thus perpendicular to the scattering plane, the differential cross-section is independent to the scattering angle (Girard M J A, Dupps W J, Baskaran M, Scarcelli G, Yun S H, Quigley H A, Sigal I A and Strouthidis N G, "Translating Ocular Biomechanics into Clinical Practice: Current State and Future Prospects", Curr. Eye Res. 40(1), 1-18 (2015)), thus configurations with orthogonal illumination-detection paths have the same differential cross-section as the epi-detection. However, the angled geometry will result in diminished geometrical efficiency per single point (i.e. excluding the advantage due to the massive parallelization of the measurement). The collected scattering power can be written as $P=I_{ill} \cdot V \cdot \Omega \cdot R$, where $I_{ill}$ is the intensity of the illumination light, V is the interaction volume of the scattering, $\Omega$ is the collected solid angle, and R is the scattering coefficient, which has a unit of $m^{-1}$ and can be considered as constant here. In orthogonal configuration, the interaction volume can be approximated by a cylinder with radius $r=0.61\lambda/NA_{col}$, and length $l=0.61\lambda/NA_{ill}$, where $NA_{col}$ and $NA_{ill}$ are the NA of the illuminating objective lens and collecting objective lens, respectively. The collected solid angle depends on the collecting numerical aperture $\Omega=\pi NA_{col}^2$. Therefore, the collected scattering power is $P_{90}=I_{ill} \cdot R \cdot \pi^2 \cdot 0.61^3 \cdot \lambda^3/NA_{ill}$. For epi-configuration, instead, the interaction volume is approximately $0.61^2\lambda^3/NA_{epi}^4$, where $NA_{epi}$ is the NA of the objective lens, and the collected solid angle is $\Omega=\pi NA_{epi}^2$. Thus, the collected scattering power is $P_{epi}=I_{ill} \cdot R \cdot \pi^2 \cdot 0.61^2 \cdot \lambda^3/NA_{epi}^2$. With same illumination intensity, the ratio of the collected power between two configurations turns out to be $\eta=P_{90}/P_{epi}=0.61 \cdot NA_{epi}^2/NA_{ill}$. In orthogonal configurations, low $NA_{ill}$ is usually preferred in order to generate a long illumination beam line uniform across the field of view. For example, we used $NA_{ill}=0.0175$ that corresponds to a 1.737 mm usable Rayleigh range. Comparing our particular experimental configuration with epi-configuration with $NA_{epi}=0.1$ (providing the same resolution in x-direction), the ratio is 34.8%. This calculation is consistent with the prediction by other work (Scarcelli, G., Kim, P. & Yun, S. H. "In vivo measurement of age-related stiffening in the crystalline lens by Brillouin optical microscopy", Biophysical Journal 101, 1539-1545 (2011)) where a different combination of objective lens was used. Importantly, this calculation is consistent with the experimental results in FIG. 2 and with other epi-detection results (Guilluy, C., et al. "Isolated nuclei adapt to force and reveal a mechanotransduction pathway in the nucleus". Nature Cell Biology 16, 376 (2014)). The scattering efficiency in orthogonal and epi-detection is determined by the overlap between the illumination volume and detection volume, therefore one can design angled-geometries to be as efficient as epi-detection per single point measurement to maximize the parallelization advantage. Including the line parallel detection, the multiplex Brillouin spectroscopy can accomplish the scan of a mm-sized sample with few-micron resolution within tens of seconds compared to greater than one hour in epi-detection. The measurable size along the beam line is determined by both the illumination NA and the pixel number of the camera. The spatial resolution is determined by the detection NA (x-direction, along the beam line) and illumination NA (y- and z-direction).

In terms of background rejection, the angled configuration has inherently less background noise than epi-detection. In common confocal configuration, back reflections of the illuminating light are easily coupled into the spectrometer and contribute to the background noise. In the line-scanned configuration, because the illumination and detection path are arranged orthogonally, the back reflection can be completely avoided. Furthermore, since only the region that is illuminated by the line beam is excited, the line-scanned configuration has similar function of optical sectioning as confocal configuration. On the other hand, since only one-stage VIPA is used, the extinction ratio of the spectrometer is limited. This makes it challenging to measure interfaces or optically opaque samples, such as intralipid medium or tissue. To improve the overall extinction ratio of the instrument, the line-scan configuration can be combined with existing methods that can suppress the background noise such as apodization, narrow band-pass filtering, and gas-chamber narrow absorption filtering.

Another aspect of the current invention relates to a system and method for classifying living cells based on subcellular physical (mechanical) properties. By way of example and without limitation, the cells to be classified may be human, animal, or plant cells. The subcellular physical information is obtained from the spectral analysis of the Brillouin light scattering related to the acoustic properties inside the cells. The classification can be based on either cell population or individual cells. In one embodiment, cells can be analyzed in suspended conditions, adherent to 2D substrates, and/or cultured within 3D synthetic/natural extracellular matrices. In yet another embodiment, cells can be analyzed in static conditions or via cell flow.

In one embodiment, the cells can be cultured and prepared in vitro and delivered to a probe beam using microfluidic devices. The subcellular information at different regions of the cells can be acquired in several settings taking advantage of standard or custom microfluidic devices. Cells can be analyzed in nearly all settings associated with flow cytometry or other cell analysis techniques. By way of example and without limitation, cells can be measured while flowing inside a microfluidic channel, mapped when they stay still in suspension, encapsulated in droplets of 3D gels or other extracellular matrices according to known methods, and/or while forming cell aggregates. Alternatively, with or without microfluidic devices, cells can be analyzed in other settings (such as in dishes, or flasks, or plate arrays) while adherent onto substrates, or within 3D gels or while forming aggregates by guiding Brillouin acquisition of subcellular information with a bright-field or confocal imaging modality. Based on the acquired physical phenotyping, different types of cells or same type of cells in different phases of the cell cycle can be distinguished. In one embodiment, cell response to drugs can be analyzed. The analysis can be performed on either population of cells or on individual cells.

Figure 12:
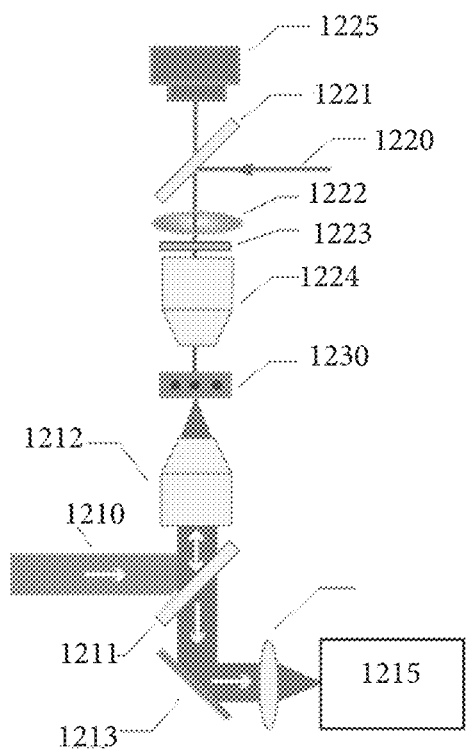
FIG. 12 illustrates a Brillouin spectroscopy setup for a point-by-point scanning mode according to one embodiment of the current invention.

FIG. 12 illustrates an exemplary embodiment of the current invention resulting from a novel combination of an epi-detection path to excite/collect Brillouin signal, a monitoring imaging modality, a microfluidic device (or other cell plating device), a Brillouin spectrometer and a computer with software that links all of these sub-components. A first incoming illuminating beam 1210 is focused onto one spot inside a microfluidic device 1230 by using a beam splitter 1211 and an objective lens 1212. The illuminating laser beam 1210 may be a laser beam. In one embodiment, the first incoming laser beam 1210 is focused into spot of 1 to 10 µm. The backward Brillouin scattering light is collected by the same objective lens 1212 and guided to a Brillouin spectrometer 1215 via the beam splitter 1211, a reflected mirror 1213, and a coupling lens 1214. The Brillouin spectrometer 1215 is a device that can measure the Brillouin frequency shift accurately. One example of the Brillouin spectrometer 1215 is disclosed in Scarcelli Polachech 2015 Nature Methods Above the microfluidic device 1230, there is a bright-field microscope consisting of a second light source 1220 (usually has a different wavelength from laser beam 1210), a beam splitter 1221, a tube lens 1222, an objective lens 1224, and a 2D image recording device 1225. The purpose of this microscope setup is to monitor the flowing status of the cells inside the microfluidic device 1230. In one embodiment, the microscope setup further contains a spectral filter 1223, which blocks the light from the laser beam 1210, but allows the light from a light source 1220 to pass. The objective lenses 1212 and 1224 are adjusted to make sure the focused spot from the objective lens 1212 is on the image plane of the objective lens 1224.

In one embodiment, a software interface may be used to synchronize the bright field image obtained by the 2D image recording device 1225 and the Brillouin signal of the Brillouin spectrometer 1215. By doing this, the Brillouin signal can be assigned to a right location of the measured sample.

Figure 13:
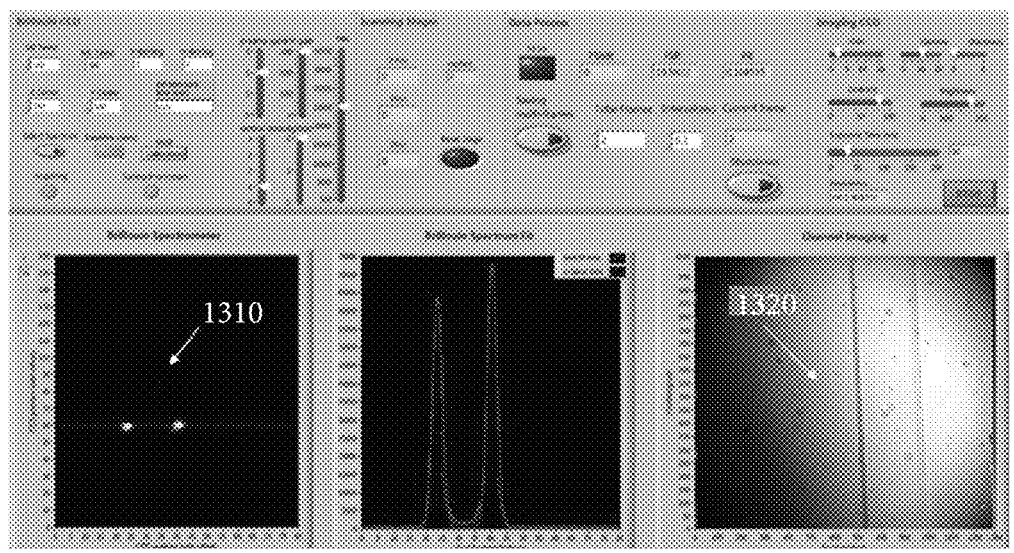
FIG. 13 illustrates a snapshot of a controlling interface associated with the Brillouin spectroscopy setup according to FIG. 12.

FIG. 13 illustrates a snapshot of the interface used in conjunction with the Brillouin spectroscopy setup of FIG. 12. The primary function of the interface is to simultaneously record a raw Brillouin signal 1310 (spatio-spectral pattern) and bright-field image 1320 of the microfluidic device having cells therein. The two white dots 1310 are Brillouin signals (spatio-spectral pattern), and the distance between the dots represents the Brillouin peaks. The distance from the laser line to the Brillouin peak is the desired frequency shift. In this representation, with the proper calibration provided here, the Brillouin shift can be measured by calculating the distance between two Brillouin peaks; in this case, shorter distance between the two peaks corresponds to bigger frequency shift and thus higher stiffness).

In FIGS. 14a-14f, a non-limiting example of how the Brillouin signal detection could be implemented in practice is illustrated. Specifically, FIGS. 14a-14c are snapshots of both a raw Brillouin signal (spatio-spectral pattern) and a bright-field image acquired simultaneously at 0.85 sec, 1.35 sec, and 1.65 sec, respectively. The snapshots show a cell flowing inside a channel, from top to bottom. The circle 1402 indicates the location of the illuminating (probe) beam spot that the cells are crossing. FIGS. 14d-14f show time traces of the Brillouin frequency shift calculated from the raw Brillouin signal of FIGS. 14a-14c. From the synchronized images of FIGS. 14a-14c, the original location of the Brillouin signal can be identified without ambiguity. Beyond assigning a Brillouin frequency shift to a specific subcellular location, this capability can be also used to guide a Brillouin probe beam to specific locations by incorporating image processing techniques and either translating the cell container or controlling the position of the Brillouin probe beam.

In one non-limiting embodiment, the microfluidic device 1230 as shown in FIG. 12 can be placed on a 2D translational stage in order to align cells to a focused probe beam spot. By way of example and without limitation, the microfluidic device 1230 may be a straight channel with rectangular cross-section or a channel with circular cross-section as in the majority of flow cytometers. If the size of the channel (by way of example, 100 µm by 100 µm) is much larger than the size of the cell (by way of example, 10 µm to 20 µm in diameter), cells may flow through the microfluidic device 1230 at random locations thus diminishing accuracy and potentially throughput of the measurement. In one embodiment, in order to align the cells along the same trace inside the channel so that every cell can be probed by the illuminating beam 1210, hydrodynamic focusing techniques called sheath flow can be implemented. This is an effective way to ensure that the center of each cell is consistently aligned to the focused spot of the probe beam 1210.

FIGS. 15a-15b illustrate a comparison of experimental data obtained by using the sheath flow technique (FIG. 15b) and obtained without using the sheath flow technique (FIG. 15a). By adjusting the flow rate and acquisition time of the spectrometer 1215, several locations of one cell can be probed when the cell passed across the light beam 1210. For the plot in FIG. 15a-15b, the average of all the Brillouin frequency shifts acquired within a cell was calculated to describe the average stiffness of a single cell. Therefore, in FIG. 15a-15b, each data point of the histogram represents one cell. The results show that the spread (linewidth of the distribution) of the measured data is about 40% narrowed by using the sheath flow technique because the artificial broadening caused by a non-sheath flow is removed. In one non-limiting embodiment, the NIH 3T3 cell line was used in the experiment.

In yet another embodiment, a second approach, named as image-guided alignment, may be used to align the flowing cell to the focused spot of the laser beam 1210. The schematic of the concept is shown in FIG. 16. This approach can be also implemented within the setup shown in FIG. 12 with the following modifications. In FIG. 12, the focused spot of the laser beam 1210 locates in the center of the field of view of the microscope 1212. In FIG. 16, however, the focused spot 1620 was moved to the bottom of the microfluidic channel 1610 and set at the middle point along the x-direction, i.e., at $x_0$. Suppose a cell 1630 is flowing along y-direction (from top to bottom), once it appears in the field of view, its location ($x_1$) and the horizontal shift ($x_0$-$x_1$) with respect to the focused spot 1620 can be determined. Then the translational stage carrying the microfluidic channel 1610 can be either automatically or manually moved to align the cell 1630 to the focused spot 1620 perfectly. Alternatively, in yet another embodiment, the Brillouin probe beam can be adjusted with laser scanning accessories (e.g. galvanometer scanners, polygons) or other well-known beam positioning techniques. The success of this approach is based on two conditions. First is that all of the flowing experiment is laminar flow, which assures that the cells will not drift laterally, but keep their trace once they enter the channel. Second is that the feed-forward algorithm that adjusts the location of the cell and the probe is faster than the flow speed so that there is enough time to do the position adjustment of the channel. A representative experimental result obtained by using the Brillouin spectroscopy setup of FIG. 12 is shown in FIG. 17a. Cells were cultured and suspended in a buffer solution right before the experiment. In one embodiment, Phosphate-Buffered Saline (PBS) was used as a buffer solution. By adjusting the flow rate, five to ten positions within each cell were probed when the cell passed across the light beam. In this case, all of the measured data points were used to plot the histogram graph in FIG. 17a. The histogram of FIG. 17a consists of three parts, which are outlined by three solid curves 1702, 1704, and 1706. The first peak 1704 is the signature of the PBS, which can be easily recognized, located, and removed as shown in FIG. 17b. The appearance of the PBS's signature in the measured data is expected since the light beam 1210 will only probe buffer solution within the time interval between two adjacent cells. In one non-limiting embodiment, NIH 3T3 cell line may be used for the cell flowing experiment as described above.

To extract subcellular information, curve-fitting methods can be used to extract the signature of the cells from FIG. 17a. A linear superposition of three Gaussian distributions 1702, 1704, and 1706 was used to fit the original histogram. Since the signature of the PBS solution 1704 can be well determined by fitting the data of FIG. 17b in advance, this information can be used as known parameters of the fitting. After best fitting the original histogram of FIG. 17a by the dashed curve, the information of the cells was obtained by subtracting the signature of the PBS solution 1704, as shown in FIG. 17c. It is clear that the histogram of FIG. 17c consists of two peaks, which are the superposition of two Gaussian distributions 1708 and 1710. In fact, Gaussian distributions 1708 and 1710 represent mechanical signatures from different regions (i.e., cytoplasm and nucleus) within the cells.

Figure 18A:
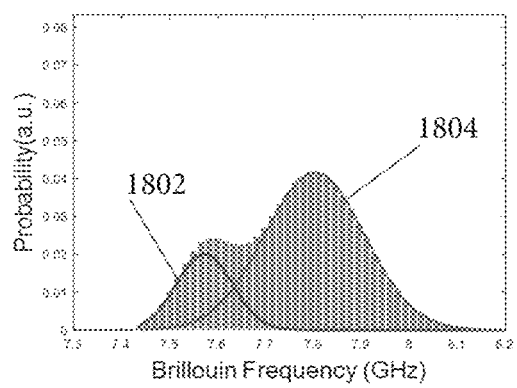
FIG. 18a illustrates a cell spectral analysis resulting from measurements obtained by using the Brillouin spectroscopy setup according to FIG. 12.
Figure 18B:
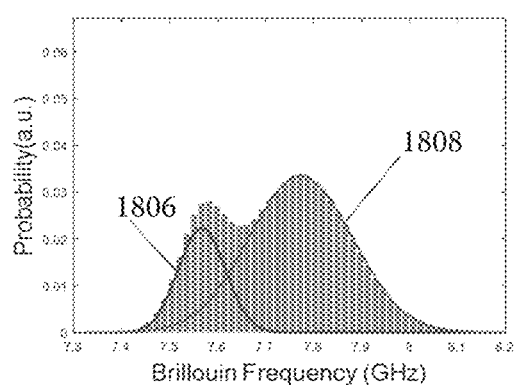
FIG. 18b illustrates a spectral analysis resulting from 2D Brillouin cell images.

To verify that the flow data in FIG. 17a truly represents the mechanics of a cell population, a direct comparison between flow data of cell population and 2D images of a set of cells was done. First, the cells were delivered into the microfluidic device 1230 of FIG. 12, and then stopped for a couple of minutes to make sure the cells are suspended inside the channel. As a comparison, a flow experiment based on obtaining Brillouin frequencies at multiple points within the cells and using the same cell line prepared with identical methods was done by using the Brillouin spectroscopy setup of FIG. 12. FIG. 18a is a histogram illustrating the distribution of Brillouin frequency shifts measured for a collection of points along the line where the cells flowing through the channel cross the laser. In one embodiment, five hundred seventy seven (577) cells (3546 subcellular points) were measured. The histogram of FIG. 18a is fitted by a superposition of two Gaussian distributions 1802 and 1804. FIG. 18b is a histogram resulting from the 2D Brillouin images of flowing cells fitted by a superposition of two Gaussian distributions 1806 and 1808. In one embodiment, twenty nine (29) cells, including 4378 total subcellular points, were measured. It is shown that the histograms in FIGS. 18a and 18b share the same features, including the two-peak profiles and the frequency shifts of each peak. It is noted, that the number of cells and measurement as specified above is not limiting and any number of cells and measurements can be used to obtained the histograms of FIGS. 18a-18b.

Figure 19A:
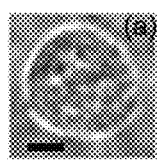
FIGS. 19a, 19b, and 19d illustrate bright-field image, fluorescence image, and Brillouin image of the same cell, respectively.
Figure 19B:
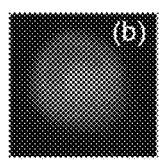
Figure 19C:
FIG. 19c illustrates the merged bright-field image of FIG. 19a and fluorescence image of FIG. 19b.
Figure 19D:
Figure 19E:
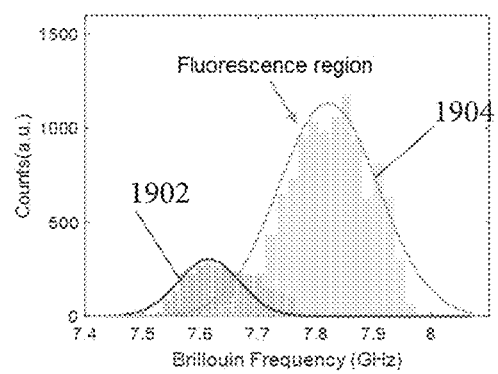
FIG. 19e illustrates a histogram of both the nucleus and cytoplasm plotted together based on the image of FIG. 19c.

Furthermore, it was verified that the two peaks of FIG. 17c corresponded to the mechanical signature of cytoplasm/cytoskeleton and nucleus. Fluorescence dye was used to stain only the nucleus of the cell, and then both the bright-field/fluorescence image (FIGS. 19a and 19b) and 2D Brillouin image (FIG. 19d) of the same cell were acquired. By comparing the image of FIG. 19c obtained by merging the images of FIGS. 19a-19b with Brillouin 2D image of FIG. 19d, nucleus can be separated from cytoplasm. The histogram of both the nucleus and cytoplasm are plotted together in FIG. 19e, where the peak 1904 is from the nucleus (corresponding to fluorescence region of FIG. 19b) and the peak 1902 is from the cytoplasm (corresponding to non-fluorescence region of FIG. 19b). Based on the comparison between FIG. 19e and FIG. 17c, it is concluded that the mechanical signature of the nucleus and cytoplasm can be distinguished in a cell population by a flow experiment using the Brillouin spectroscopy setup of FIG. 12 obtaining Brillouin frequencies at multiple points within the cells as the cells cross the probe beam. The combined fluorescence/Brillouin configuration can be used to accurately assign or image-guide Brillouin acquisition of specific subcellular components labelled with fluorescence.

In another aspect of the current invention, the capability to classify cells based on subcellular physical (mechanical) phenotyping is demonstrated. For example, the effect of Cytochalasyn D (CytoD) on cells was analyzed. It is widely accepted that the overall stiffness (deformability) of a cell is determined by both the cytoskeleton and nucleus (Fletcher D A, Mullins R D, "Cell mechanics and the cytoskeleton", Nature 463, 485-492 (2010)). The cytoskeleton consists of three main polymers: actin, microtubules, and intermediate filaments. The F-actin is the polymerized state of actin and has a dominant role in controlling cell shape and mechanical properties. Therefore, the polymerization and de-polymerization of F-actin generate directed force that drives changes in cell shape and stiffness. CytoD is a drug that inhibits the polymerization of the F-actin. It was reported that F-actin will be dramatically reduced in attached cells treated with CytoD as a result the cell overall will decrease its stiffness (Wakatsuki T, Schwab B, Thompson N C, Elson E L. "Effects of cytochalasin D and latrunculin B on mechanical properties of cells.", J Cell Sci. 114, 1025-1036 (2001)). At a subcellular level both nucleus and cytoskeleton will decrease stiffness as actin is present in both. Moreover, because nucleus and cytoskeleton are mechanically connected, the nucleus sustains pre-stress from the cytoskeleton (Wang N, Tytell J D, Ingber D E. "Mechanotransduction at a distance: mechanically coupling the extracellular matrix with the nucleus", Nat Rev Mol Cell Biol. 10, 75-82 (2009)). Thus, the disruption of the F-actin should also reduce the pre-stress so that eventually soften the nucleus (Chalut K J, Hopfler M, Lautenschläger F, Boyde L, Chan C J, Ekpenyong A, Martinez-Arias A, Guck J. "Chromatin decondensation and nuclear softening accompany Nanog downregulation in embryonic stem cells", Biophys J. 103, 2060-2070 (2012)).

Figure 20A:
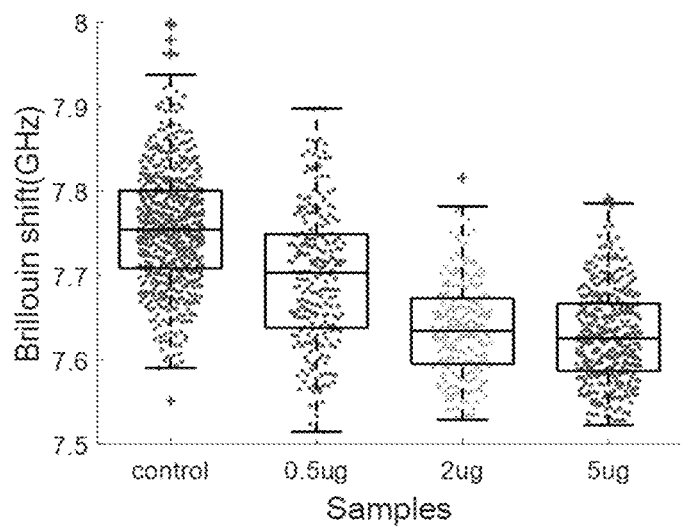
FIGS. 20a-20e illustrate a cell spectral analysis that is indicative of the effect of Cytochalasyn D on a nucleus.
Figure 20B:
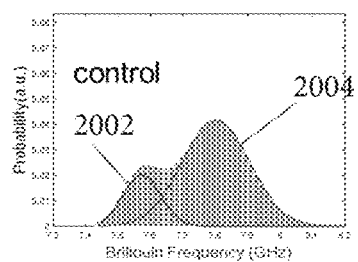
Figure 20C:
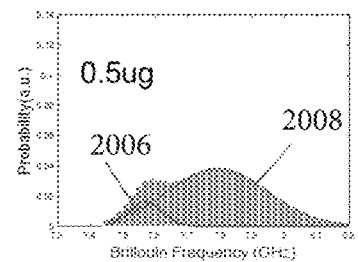
Figure 20D:
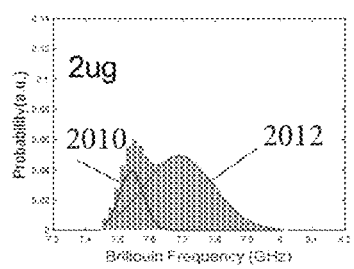
Figure 20E:
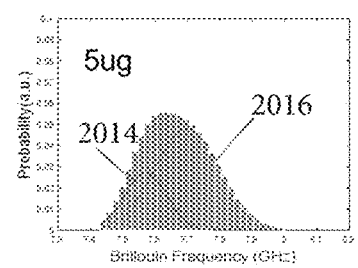

In one embodiment, CytoD is applied on cells and then detached using trypsin. After that, the treated cells are re-suspended in PBS and measured in the setup of FIG. 12. In order to observe the doses dependence, three doses of CytoD were used. By way of example and without limitation, the CytoD doses were 0.5 ug/ml, 2 ug/ml, and 5 ug/ml. The treated cells (279, 232, and 577) were probed for each doses and untreated cells (268) were probed for control. The average value over the whole cell was used to represent mechanical phenotyping of the cell. The results in FIG. 20a indicate the dose dependent effect of CytoD on the stiffness of the cells. Thus, the average Brillouin frequency shift value over the whole cell can be used to obtain high-throughput mechanical phenotyping. In one non-limiting embodiment, NIH 3T3 cell line was used to carry out the experiment.

Beyond the averaged cell values, the method described with the reference to FIGS. 17*a*-17*c* can acquire subcellular information. As shown in FIGS. 20*b*-20*e* corresponding to different doses of CytoD, the Brillouin frequency shift of peaks 2004, 2008, 2012, and 2016 got smaller and thus moved to the left from FIG. 20*b* to FIG. 20*e*. This is an indication that the nucleus is getting softer with the treatment of higher dose of CytoD. On the other hand, it is noted that peaks 2002, 2006, 2010, 2014, which represent the cytoplasm, have almost no change in this experiment. This is because the trypsinization step used to detach cells from the flask substrate has disrupted all F-actin stress fibers, so that there is little measurable effect on the cytoskeleton for the suspended cells. It was verified that in adherent cells the cytoskeletal stiffness is markedly reduced.

Figure 21:
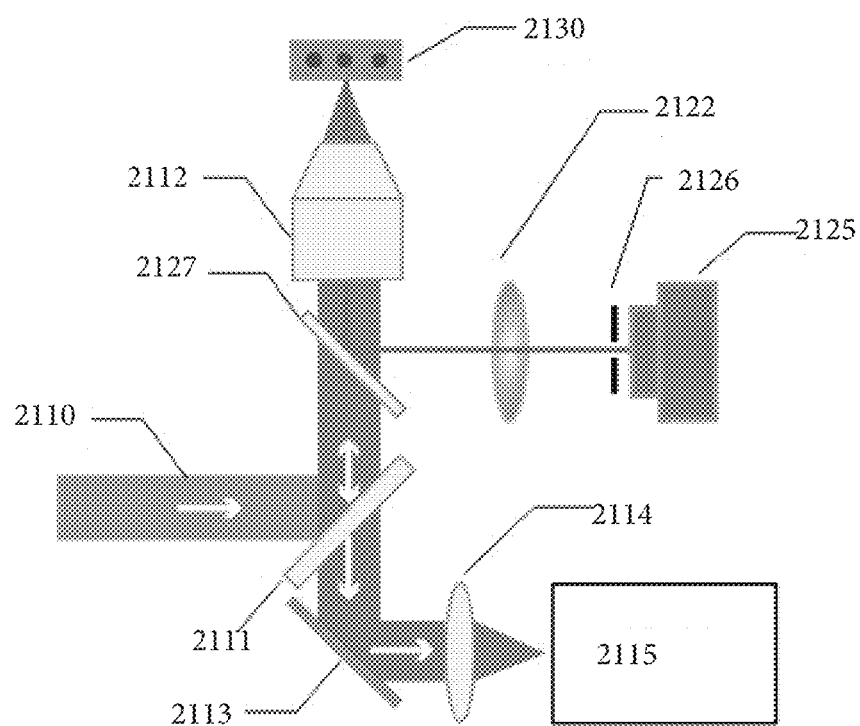
FIG. 21 illustrates a Brillouin spectroscopy setup for the point-by-point scanning mode according to another embodiment of the current invention.

FIG. 21 illustrates a Brillouin spectroscopy setup according to another embodiment of the current invention. In this embodiment, a second optical modality is added to acquire a co-registered confocal fluorescence image of the cell simultaneously when the cell is probed by the Brillouin beam. The second optical modality may comprise a dichroic mirror 2127, a tube lens 2122, a pinhole mask 2126, and a photo-detector 2125. The dichroic mirror 2127 will let the laser beam 2110 and the Brillouin signal pass through but reflects the fluorescence light. Compared with the bright-field microscope of FIG. 12, the confocal configuration has better transverse and lateral optical resolution by rejecting fluorescence light from the out-of-focus plane. In practice, fluorescently labelled cells can be used to identify a sub-region of a cell (e.g., nucleus) and the focused spot of laser beam 2110 can be used to directly excite fluorescence emission. Then, the confocal configuration is used to detect the fluorescence emission light by a camera 2125. Based on the intensity of the fluorescence emission light, one can accurately determine the location of the focused spot (and thus the Brillouin signal) inside the cell so that the Brillouin signal can be assigned to a targeted point. This modality can also be used to guide the Brillouin beam to a specific region of the cell during measurement. In yet another embodiment, in addition to the inverted configuration, the upright configuration of the confocal microscope can be used. In this case, the confocal configuration will be on the top of the microfluidic device 2130. The fluorescent information can also be used to estimate the amount of non-cellular medium (e.g. PBS) present in the three-dimensional imaging voxel in order to calibrate measurements at the edge of a cell.

Figure 22:
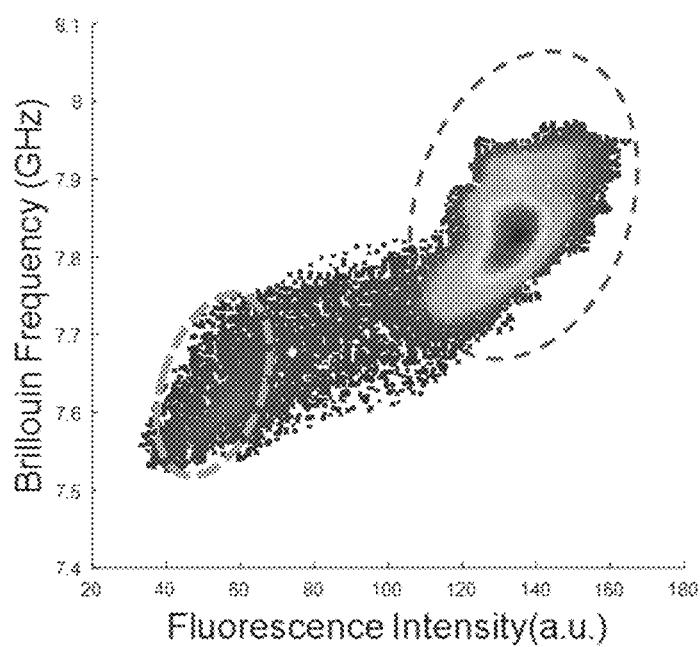
FIG. 22 illustrates a cell image obtained by the Brillouin spectroscopy setup of FIG. 21. Each point in the image represents one measurement taken in a certain region within the cell, and the different shades encode the relative density of the data points.

The image in FIG. 22 is obtained by using the Brillouin spectroscopy setup according to the embodiment of FIG. 21, but with bright-field fluorescence rather than confocal microscopy. Fluorescence dye was used to stain the nucleus of the cells subsequently delivered into the microfluidic device 2130. Once the cells stayed still in suspension, a 2D mapping of a single cell was performed by moving the microfluidic device. Since Brillouin beam spot and fluorescence light are overlapped with each other in space, the Brillouin signal can be linked to the fluorescence intensity for each measured point. One possible way of representing the result is shown in FIG. 22. Each point represents one measurement taken in a certain region within a cell, and the different colors encode the relative density of the data points. From the scattering plot, one can clearly tell the location of each Brillouin signal according to the fluorescence intensity plotted on the abscissa. For example, the dashed circles indicate the measured points from the nucleus (fluorescence region) and cytoplasm (non-fluorescence region), respectively.

As an example of classifying cells using the embodiment of FIG. 21, effect of CytoD on the cells was analyzed. Both Brillouin and fluorescence 2D imaging of cells with and without treatment was done, and the method of FIG. 22 was used to analyze the data. The result is shown in FIGS. 23*a*-23*b*, in which (a) and (b) are results of control group and CytoD treated group, respectively. It is observed that the nucleus is much softened after the cell is treated with CytoD.

In the embodiments of FIGS. 12 and 21, the Brillouin signal is acquired in a point by point-scanning mode, which is a limitation of the overall throughput. As such, it may be difficult to acquire enough subcellular points per cells to analyze individual cells. Thus the embodiments of FIGS. 12 and 21 are useful for cell population analysis, but may be less powerful for single cell mechanical phenotyping and thus would not be suitable for cell sorting applications. One solution to this issue is to lower the flow speed to have enough subcellular points for single cell analysis. Another solution is to employ more than one spectrometer to measure more than one location at one time. Alternatively, the Brillouin spectroscopy setup according to FIG. 7 can measure multiple points of a cell at the same time. The optical arrangement of FIG. 7 has one critical modification in comparison to the arrangements of FIGS. 12 and 21. The main change here is that a pair of the objective lenses 713 and 714 is utilized at high resolution to straighten the curved Brillouin spectra pattern recorded by the CCD camera. This is critical because it will ensure that acquired Brillouin signal is accurately assigned to its corresponding location along the illuminating line beam. Specifically, the beam from a laser source 710 is first guided by a mirror 724 and then focused by an objective lens 711 to be an illuminating line beam in x-direction. The line beam shines into the channel of a microfluidic device 712 from its edge. The cells can pass through the line beam by flowing along y-direction. The Brillouin scattering signal excited by the line beam is detected by a parallel configuration of a Brillouin spectrometer, which consists of a pair of objective lens 713 and 714, a collimated lens 715, a cylindrical lens 716, a dispersion device (i.e., VIPA) 717, cylindrical lenses 718 and 719, a mask 720, a spherical lens 722, and a high-sensitive CCD camera 723.

Different from the spectrometers of FIGS. 12 and 21, the multiplexed Brillouin spectrometer of FIG. 7 can simultaneously obtain Brillouin signals from many points along the illuminating line beam. For example, by choosing proper objective lenses and adjusting the optics within the spectrometer, the resolution of less than 1 μm can be achieved in x-direction. Since the typical size of a cell is around 10 to 15 μm, around 10 points for one shot and up to greater than 100 points for a single cell when it is flowing through can be captured. This dataset would surely give enough information to obtain the subcellular mechanics of a single cell. The embodiment in FIG. 7 thus offers one a more effective way to classify a single cell based on its subcellular mechanical phenotyping. In some embodiments, in addition to the right angled arrangement of the illumination path and detection path, the setup of FIG. 7 can also work at any angle greater than 0°, including arrangement angles of 45° and 60°.

FIG. 24 shows a conceptual sketch of the embodiment of FIG. 7. The illumination laser line 2410 illuminates the microfluidic channel 2430 from its left edge (x-direction), and a cell 2420 flows inside the channel along y-direction. As the cell 2420 encounters the laser line 2410, Brillouin signals from the illuminated region of the cell 2420 will be acquired simultaneously. When the cell passes through, the whole cell body can be scanned by the line beam. Eventually, a 2D image 2440 of the cell 2420 can be reconstructed, as shown in FIG. 24.

The embodiment of FIG. 7 can be further improved by adding filtering elements to remove spurious light from laser reflected or scattered from the cell, or the channel. For this purpose, the Fabry-Perot filter can be used. The Fabry-Perot filter is actually an etalon that allows light with selected frequency to pass and block the others. By proper design of the filter, the transmission peak of the filter can be adjusted to overlap with the Brillouin signal. The spurious light has a different frequency from Brillouin signal so that will be suppressed. However, the method of FIG. 7 may introduce alignment issues and potential artifacts that should be resolved with an accurate calibration.

Alternatively, an absorption gas chamber can be used (Piironen P, Eloranta E W. "Demonstration of a high-spectral-resolution lidar based on an iodine absorption filter", Opt. Lett. 19, 234-236 (1994)). The gas chamber does not introduce spectral dispersion via the redirection of beam and thus is highly suitable for parallel spectrometer. The gas chamber is usually fabricated from glass and contains vapors from specific atomic element which has a well-defined absorption spectrum. The light passes through the gas chamber via entrance and exit windows without introducing any optical distortion. The absorption gas has a very narrow (less than 1 GHz) molecular absorption spectra at specific optical wavelength. By properly choosing the absorption gas, a gas chamber whose absorption line overlaps perfectly with the wavelength of the laser source 710 can be designed. For example, the gas chamber could be placed between the lenses 712 and 713, and the spurious light (with the same wavelength of laser source 710) will be absorbed while the Brillouin signal will pass through. The linewidth of the absorption spectrum is so narrow that any small drift of the laser's frequency will make the gas chamber ineffective. In order to make the gas chamber work well with the embodiment of FIG. 7, it is necessary to lock the wavelength of the laser source to the absorption line of the gas chamber. As an example, FIG. 25 shows a measured absorption spectrum of a gas chamber containing Rubidium gas. This gas chamber works at the wavelength of 780.24 nm, and the result shows that when the chamber was heated up to 94.5 degree C., the peak absorption is about 34 dB with an insert loss of 2 dB. The gained spectral extinction allows for measuring biological samples that have a strong background noise.

Example 4

Figure 26:
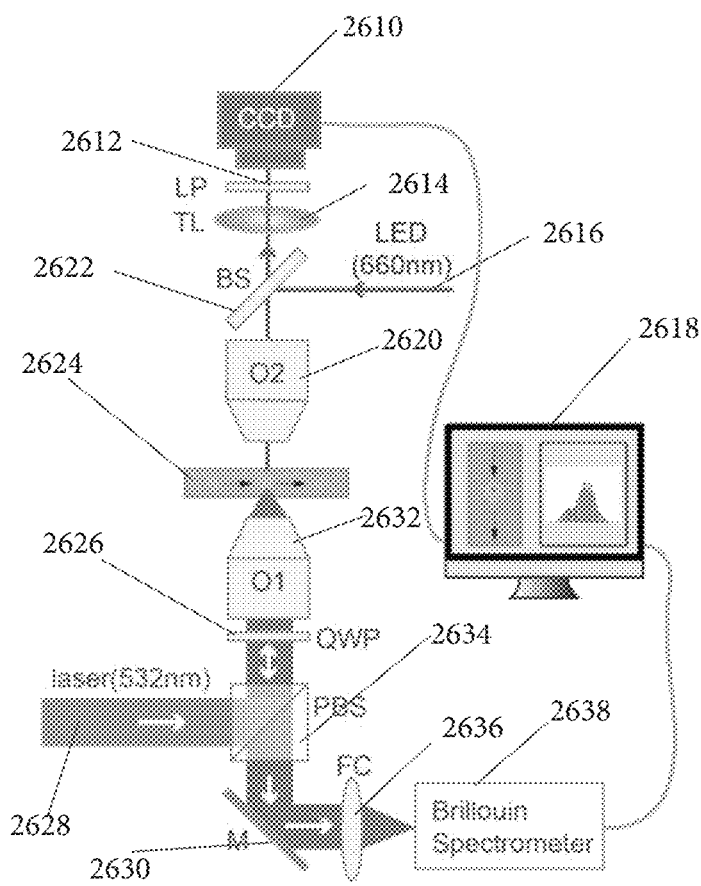
FIG. 26 illustrates a Brillouin spectroscopy setup for the point-by-point scanning mode according to another embodiment of the current invention (used in Example 4).

An exemplary setup of the current invention is shown in FIG. 26. A vertically-polarized laser beam 2628 is first reflected by the polarized beam splitter (PBS) 2634 and focused into the center of a microfluidic channel 2624 from the bottom side by objective lens 2632. In one embodiment, a 11-mW single-mode linearly-polarized 532-nm cw laser (Torus, Laser Quantum) was used as a light source to excite Brillouin scattering. Due to the quarter-wave plate (QWP) 2626, the focused beam was circularly polarized. The backward scattered light was collected by the same objective lens 2632 and passed through the QWP 2626 again. The circularly-polarized light is eventually turned into horizontally-polarized one which is totally transmitted by the PBS 2634. The scatted light is then guided by a mirror 2630 and coupled into the Brillouin spectrometer 2638 by a fiber coupling lens (FC) 2636. The Brillouin spectrometer 2638 is constructed by a standard two-stage virtually imaged phased array (VIPA) in the cross-axis configuration. On the top side of the microfluidic channel 2624, a bright-filed microscope was built to monitor the flowing status of the cell inside the channel 2624. The dashed arrows indicate the flowing direction of the cells inside the channel 2624. A red LED 2616 was used for illumination and a long-pass filter is used for blocking the Brillouin beam. By way of example and without limitation, the wavelength of the LED 2616 may be 660 nm; the long-pass filter may be FEL0600, Thorlabs. The location of the focused Brillouin beam was pre-determined by removing the long-pass filter (LP) 2612. To eliminate the influence of the LED light 2616 on the Brillouin signal, a narrow-band filter was placed in front of the Brillouin spectrometer 2638. In one embodiment, a CCD camera 2610 and the Brillouin spectrometer 2638 were synchronized by a LabVIEW program so that the spectrometer's data can be assigned to the corresponding location of the measured sample. In one embodiment, during experiment, the sampling time of the spectrometer was set as 50 ms. FIGS. 27a-27d shows measurement procedures of a cell flow experiment based on obtaining Brillouin frequencies at multiple points within the cells. As the experiment is running, the Brillouin spectrometer 2638 records signals continuously. When a cell passes through the beam location (white dots indicated by the arrows), its Brillouin shift is measured.

Microfluidic Device

The chip used in the setup of FIG. 26 has a single straight channel 2624 with sheath flow configuration at the inlet. In one embodiment, the cross-section of the channel has a size of 150 μm (width) by 50 μm (depth), and the length is about 50 mm. The chip is assembled on the 2D stage of the microscope and connected to a syringe pump for delivering the cells suspension into the channel. A sheath flow technique may be used to align the cells into the center of the channel. In one embodiment, the flow velocity is about 20-40 μm/s. The overall throughput varies from about 160 to 300 cells per hour with an average of 230 cells per hour.

Sample Preparation

Cells are cultured and re-suspended in a solution of phosphate-buffered saline (PBS) without Mg2+ and Ca2+. In one embodiment, the final cell concentration is 1 to 10 million cells/ml. For chromatin decondensation experiment, old culture medium is aspirated out and replaced with 100 ng/mL trichostatin A (TSA) solution in complete growth media. Cells are then incubated for 2 hours. After incubation, cells are harvested using 0.25% trypsin-EDTA, centrifuged at 250×g for 5 minutes and re-suspended in PBS without Mg2+ and Ca2+ at approximately 2.5 million cells/mL. For fluorescent staining of nucleus, the Vybrant Dye-Cycle Ruby stain (ThermoFisher) was used and the suggested protocol was followed. In short, 1 μL stain is added to cell suspension with concentration of 0.5 million cells per mL and mixed well. The final stain concentration is 5 μM. The mixture is then incubated at 37° C. for 15-30 minutes and protected from light. Cells without washing are then ready for fluorescence experiment. In one embodiment, NIH 3T3 cell line is used for experiment.

Two-Dimensional Images of Cells

In one embodiment of the invention, cell suspension is delivered into the microfluidic channel slowly using a syringe pump. Once the cells are filled in the channel, pump is stopped. After several minutes, cells would settle down to the bottom of the channel, but still keep a rounded shape. The height of the laser beam spot is then adjusted to the center of the cell, and 2D scanning is performed in the horizontal plane by scanning the stage of the microscope. The step size of the scan is set as 0.5 µm in both dimensions. In one embodiment, NIH 3T3 cell line is used for the experiment.

Extraction of Cell's Signature from Original Flow Data

Figures 27A, 27B, 27C:
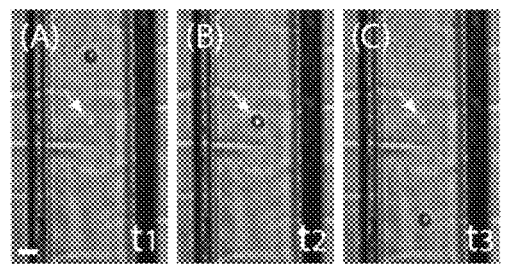
FIG. 27a-27c are snapshots of a cell flowing through a microfluidic channel at different times, the scale bar is 30 µm.
Figure 27D:
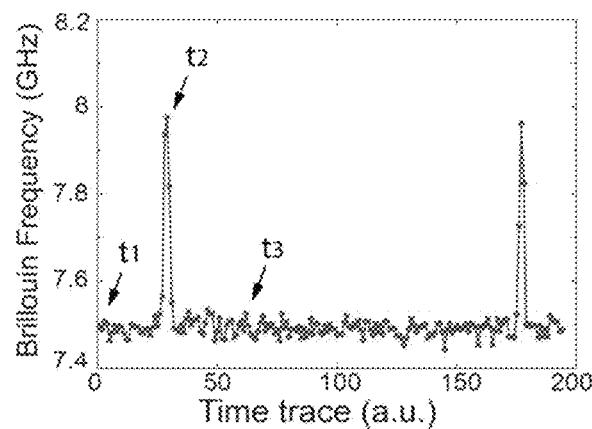
FIG. 27d demonstrates a time trace of the corresponding Brillouin signal. Dots represent measured data, and the solid line is a guide of eye.

A cell suspended in a buffer usually has a round shape. In one embodiment, the diameter of a cell ranges from 10 µm to 20 µm. Since the focused Brillouin beam has a spot size of about 0.5 µm, multiple positions can be measured when the cell flows across the beam spot. In one embodiment, during the flow experiment, the Brillouin spectrometer acquires data continuously at the rate of 20 Hz. FIGS. 27a-27d demonstrate the measurement procedures. Specifically, FIGS. 27a-27c illustrates as a cell flows through the microfluidic channel at different times (t1, t2, and t3). The scale bar is 30 µm. A white dot indicated by the arrow is the location of the laser beam spot. In FIG. 27d, time trace of the Brillouin signal is presented. Dots represent measured data and the solid line is a guide of eye.

In the data post-processing, with the aid of the bright-field images, a time window can be used to pick out the cell events from the original data stream. FIGS. 28a-28c represent the distribution of Brillouin frequency shifts measured for five hundred seventy seven (577) cells. Each data point corresponds to one measurement event of the Brillouin spectrometer measuring the Brillouin frequency shift. To preserve the mechanical information of the cells, the time window is usually wider than the lasting time of each cell event. Therefore, the mechanical signatures of both the cells and the PBS buffer are recorded and shown in FIG. 28a. The first peak 2802 of the histogram is a signature of the PBS buffer, which can be easily identified based on its Brillouin frequency shift. Then, this signature was characterized by only flowing the PBS buffer, and the result is shown in FIG. 28b. The flow data can be well fitted by a normal distribution, which indicates the Brillouin shift of 7.51 GHz with the width of 0.047 GHz. Immediately, the mechanical signature of the cells can be extracted by removing the signature 2804 of the PBS buffer from FIG. 28a, and the result is shown in FIG. 28c. The signatures of cells reveal two peaks. A linear superposition of two normal distributions 2806 and 2808 was used to fit the measured data. The results are indicated by the solid curves 2806 and 2808 in FIG. 28c, with central frequencies of 7.57 GHz and 7.80 GHz, respectively. It is known in the art, that the nucleus is usually the stiffest organelle of a cell (Friedl, P., Wolf, K. & Lammerding, J. "Nuclear mechanics during cell migration", Current Opinion in Cell Biology 23, 55-64 (2011); Girard M J A, Dupps W J, Baskaran M, Scarcelli G, Yun S H, Quigley H A, Sigal I A and Strouthidis N G, "Translating Ocular Biomechanics into Clinical Practice: Current State and Future Prospects", Curr. Eye Res. 40(1), 1-18 (2015)). Therefore, the solid curves are the signatures of cytoplasm and nucleus, respectively. This can be confirmed by staining the nucleus and comparing the fluorescent image with its Brillouin data. In addition, the volume ratio of the nucleus for 3T3 cell is reported larger than 30%, which implies a diameter ratio of cytoplasm to nucleus is around 3:7. Therefore, during the flow experiment based on obtaining Brillouin frequencies at multiple points within the cells, the signature of nucleus has more than twice chance than the cytoplasm to be measured by the Brillouin spectrometer, which is also confirmed by the amplitude of the two peaks 2806 and 2808 in FIG. 28c.

Flow Data Represents Cell Population Mechanics

Suspended cell has a rounded shape which can be approximated as a sphere for simplicity. With the help of sheath flow, the center of the cells can be aligned to the location of a laser beam spot in width direction as they flow through the microfluidic channel. Since the depth of the channel is larger than cell size, the center of cell will vary from one cell to another in depth direction. If this is the case, one line in the cross section containing the diameter of each single cell will be sampled when the cell passes across the laser beam spot. In order to ensure that the measurements of the Brillouin frequency shifts during cell flow represent the mechanics of cell population, they were compared with the images of the cross section passing through the center of cells. Specifically, 2D images of cells were obtained, as shown in FIG. 29a. FIG. 29b shows the distribution of all of the images data of FIG. 29a representing the overall mechanics of cell population fitted by a superposition of two curves 2902 and 2904 is shown. The distribution of the Brillouin flow data corresponding to a collection of points along the line where cells cross the laser is plotted in FIG. 29c and fitted by a superposition of curves 2908 and 2906. By comparing the 2D Brillouin image data of FIG. 29b with the Brillouin flow data of FIG. 27c, it is observed that both distributions have two-peak signature. More importantly, the Brillouin shifts of these two peaks for both distributions are the same, namely, 7.57 GHz and 7.80 GHz. Accordingly, it is concluded that the flow data truly reveals the mechanical properties of the cell population.

Brillouin Signatures Distinguish Nucleus from Cytoplasm

Figure 30:
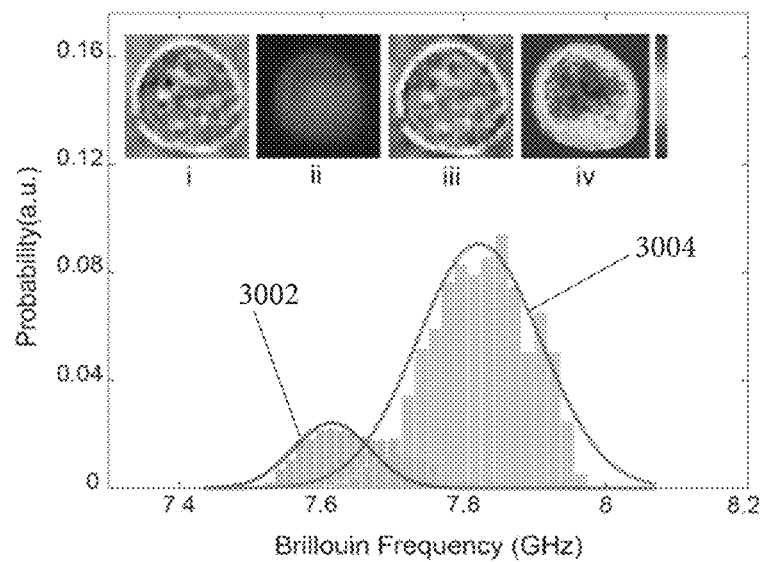
FIG. 30 demonstrates Brillouin signatures of cells verified by fluorescent images of the cells. The histograms represent Brillouin signatures from the nucleus and cytoplasm, respectively. Insert pictures: (i) bright field image, (ii) fluorescent image, (iii) merge image of (i) and (ii), and (iv) Brillouin image.

Considering suspended cells as spheres, the cells are aligned via sheath flow so that one diameter is sensed by the fixed beam spot. In practical experiment, however, since the location of cells in vertical direction varies up and down slightly, the beam spot is actually mapping a cross section passing through that diameter. In order to further verify the two-peak signature of FIG. 28c, fluorescent dye was used to stain only the nucleus of a cell. Then bright-field (I), fluorescent (II), and Brillouin 2D (IV) images were acquired, as shown in FIG. 30. By comparing a merged image (III) including the bright-field and fluorescence images with the Brillouin image, one can easily separate the Brillouin signature of nucleus from that of the cytoskeleton, as shown by histograms 3002 and 3004, respectively. Considering the small difference among the cells in a population, the distribution of the data acquired from the flow experiment based on obtaining Brillouin frequencies at multiple points within the cells should be analogous to that from the cell imaging, which is confirmed by the high similarity between FIG. 30 and FIG. 28c. Thus, it is verified that the two peaks of the flowing data in FIG. 28c correspond to the signatures of the nucleus and cytoskeleton, respectively.

Chromatin Decondensation Softens Nucleus

Chromatin is a complex of DNA and proteins that forms chromosomes within the nucleus. Its function is to efficiently package DNA into a small volume to fit into the nucleus of a cell and protect the DNA structure and sequence. Accumulating studies suggest that the condensation level of the chromatin is tightly related to the stiffness of the nucleus. For example, chromatin decondensation results in reduction in the stiffness of the nucleus. Conversely, an increase in chromatin condensation leads to a stiffened nucleus. In one embodiment, the mechanical cytometry was used to characterize the effect of chromatin decondensation caused by TSA, a histone deacetylase inhibitor.

Figure 31A:
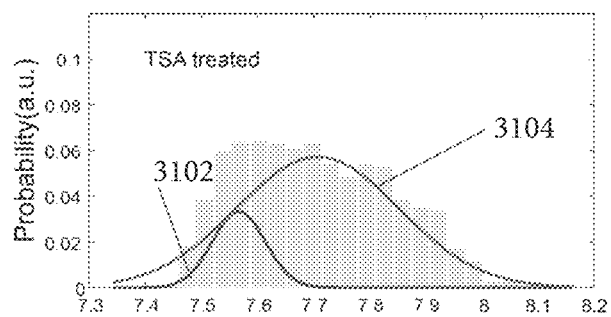
FIG. 31a-31c demonstrates experimental observation of nucleus's softening by chromatin decondensation.
Figure 31B:
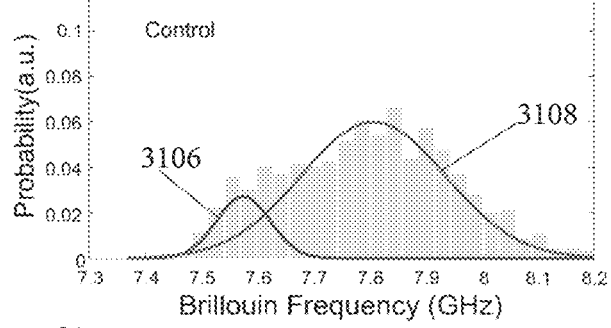
Figure 31C:
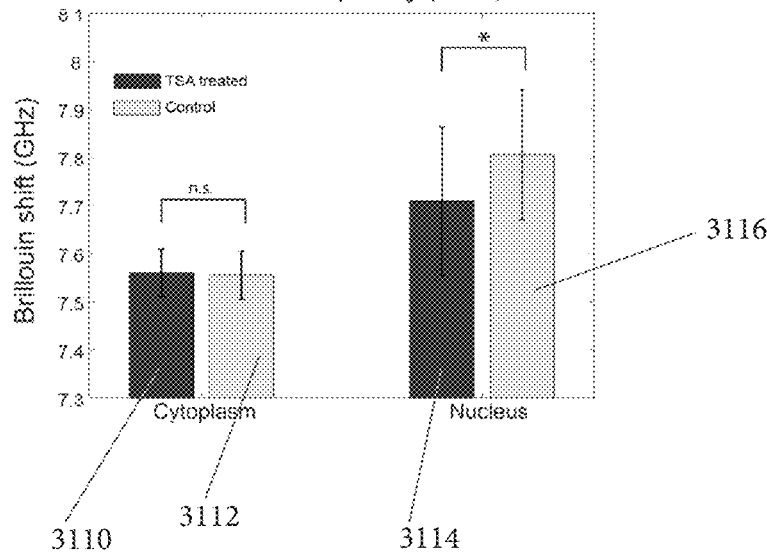

FIG. 31a-31c provides an experimental observation of nucleus's softening by chromatin decondensation. In one non-limiting embodiment, three hundred fifty six (356) and three hundred fifty three (353) cells are collected from a TSA treated and control group (not TSA treated), respectively. As shown in FIGS. 31a-31b, after the cells were treated with TSA, the Brillouin shift of the nucleus moved from 7.80 GHz (curve 3108) to 7.71 GHz (curve 3104), which indicates distinct softening of the nucleus. On the other hand, the Brillouin shift of the cytoplasm almost stayed the same (7.56 GHz (curves 3102 and 3106)) meaning that the cytoplasm was not affected by TSA. As illustrated in FIG. 31c, bars 3110 and 3112 associated with the average Brillouin shift for cytoplasm of TSA treated and control cells, respectively, have the same height, indicating no change in Brillouin frequency. In contrast, bars 3114 and 3116 associated with the average Brillouin shift for nucleus of TSA treated and control cells, respectively, have different heights, indicating a change in Brillouin frequency.

Accordingly, the mechanical cytometry according to the present invention can identify nuclear signature of cells using on-chip Brillouin technique. It provides a label-free, non-contact, and non-invasive method to measure the mechanical properties of nucleus of cell population. In one embodiment, the overall throughput is about 230 cells per hour, which is much more efficient than existing techniques such as Atomic Force Microscopy (AFM) and micropipette aspiration. Furthermore, the mechanical cytometry according to the current invention can be used to evaluate the effect of chromatin decondensation on the stiffness of the nucleus. Distinct softening after TSA treatment is found. Since the changes of nuclear stiffness involves in many important activities of cell, such as migration, differentiation and malignant transformation, the mechanical cytometry according to the current invention has a potential to find applications where an efficient and label-free characterization of nuclear mechanics of cell population is needed.

In summary, referring to FIGS. 12-31c, the method for classifying biological cells according to the present invention is based on measuring a Brillouin scattering spectrum at multiple points within each biological cell. One or more metrics related to subcellular physical properties are determined at different spatial points within the biological cells based on the measured Brillouin scattering spectrum. The biological cells are classified based on the subcellular physical properties at different spatial points within the biological cells.

In one embodiment, a histogram for the Brillouin frequency shift including each measured point within the biological cells is generated. A linear superposition of Gaussian distributions is applied to fit the histogram. Next, each peak within the histogram is determined, wherein each peak represents mechanical signatures from different regions within the cells. The physical properties at different spatial points within the biological cells are correlated to the determined mechanical signatures.

The biological sample may include biological organisms, tissues, or biological cells. In one embodiment, the biological cells are living cells. In yet another embodiment, the Brillouin frequency shift is selected as a metric. Furthermore, in one embodiment, the step of determining subcellular physical properties at different spatial points within the biological cells comprises forming an image and segmenting out parameters based on spatially-based differences in the determined physical signatures. The physical properties of the sample are selected from the group consisting of: viscoelastic modulus, density, refractive index, electrostriction, and a combination thereof.

In one embodiment, the container having the biological sample is a microfluidic channel of a microfluidic device. The biological cells flow through the microfluidic channel while the spectrum is measured.

In one embodiment, a bright-field 2D image is acquired simultaneously with the Brillouin light spectral pattern to identify an original location of the Brillouin scattering and to guide the illuminating light beam to a specific location within the microfluidic channel. In yet another embodiment, one or more Brillouin metrics are used in combination with fluorescence, Raman, forward and side scattering, to create a multi-dimensional histogram to classify biological cells. In one embodiment, a merged image including 2D bright-field and 2D fluorescence cell images is compared with a cell image based on the Brillouin frequency shift to separate a nucleus from a cytoplasm.

The Brillouin frequency shift may be measured in a point scanning mode or in a multiplexed scanning mode. The extracted physical properties obtained from within cells may refer to analysis of a single biological cell or population of biological cells.

In one embodiment, the histogram representing the Brillouin spectrum has two peaks corresponding to cytoplasm and nucleus, respectively. In yet another embodiment, modified biological cells are distinguished from intact biological cells based on subcellular mechanical characteristics of the cells defined by the Brillouin spectrum, wherein the cells are modified by drugs targeting subcellular components such as cytoskeleton or nucleus. The subcellular physical properties are used to sort cells.

Figure 32:
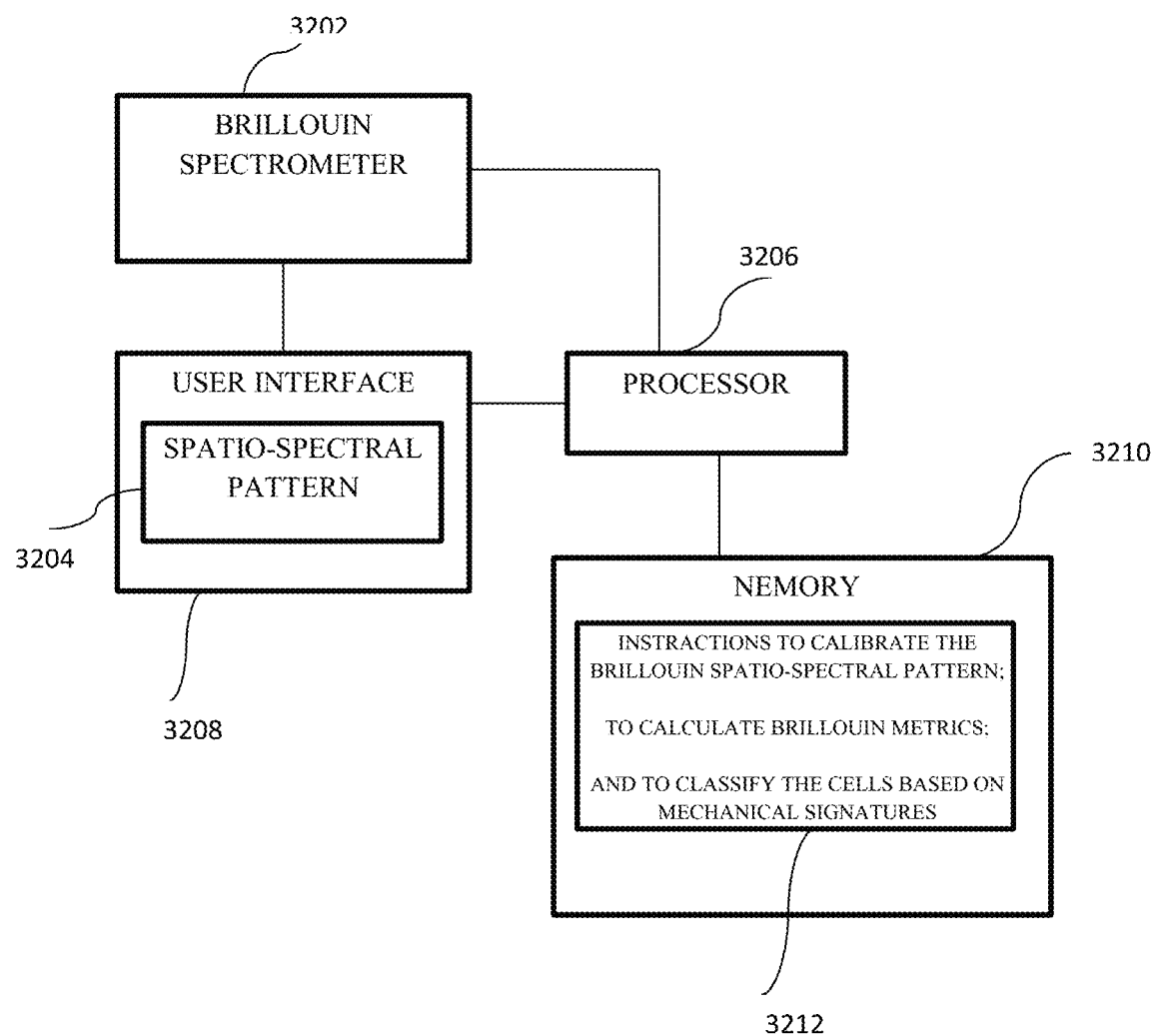
FIG. 32 is a block diagram illustrating a system according to one embodiment of the current invention.

FIG. 32 is a block diagram illustrating the system according to one embodiment of the current invention. A Brillouin spectrometer 3202 provides a spatio-spectral pattern 3404 of the Brillouin scattered light and the Brillouin light spectrum to a user interface 3208. A processor 3206 is in communication with the Brillouin spectrometer 3202, the user interface 3208, and memory 3210. The processor 3206 is configured to execute instructions in the memory 3210. In one embodiment, the memory 3210 comprises instructions for calculating one or more Brillouin metrics at each measured sample point based on the detected spatio-spectral pattern. In yet another embodiment, the memory 3210 comprises instructions for extracting one or more metrics related to subcellular physical properties at different spatial points within biological cells based on the measured Brillouin scattering spectrum and classifying the biological cells based on physical properties at different spatial points within the biological cells. Furthermore, the memory 3210 may comprise instructions for plotting a histogram for the Brillouin frequency shift and communicating the histogram to the user interface 3208; applying a linear superposition of Gaussian distributions to fit the histogram; determining each peak within the histogram, wherein the peaks represent mechanical signatures from different regions within the cells; and removing data associated with the media from the histogram.

Mechanical Properties of the Nucleus

The cellular cytoskeleton, composed of actin filament, microtubules and intermediate filaments, tightly interconnect with nucleus mechanically (Ingber D E, Wang N, Stamenovic D, "Tensegrity, cellular biophysics, and the mechanics of living systems", Rep Prog Phys. 77, 046603 (2014)). The actin filament applies tensile pre-stress on the nucleus to make it rigid. Microtubules filament acts as a compression struts to balances this pre-stress. Thus, the stiffness of the nucleus will be mediated by the balance of those two cytoskeletal filaments (Wakatsuki et al., J Cell Sci. 114, 1025-1036 (2001); Chalut et al., Biophys J. 103, 2060-2070 (2012)).

Identification of Cells Having Inhibited Actin and Microtubules

Figures 33A, 33B:
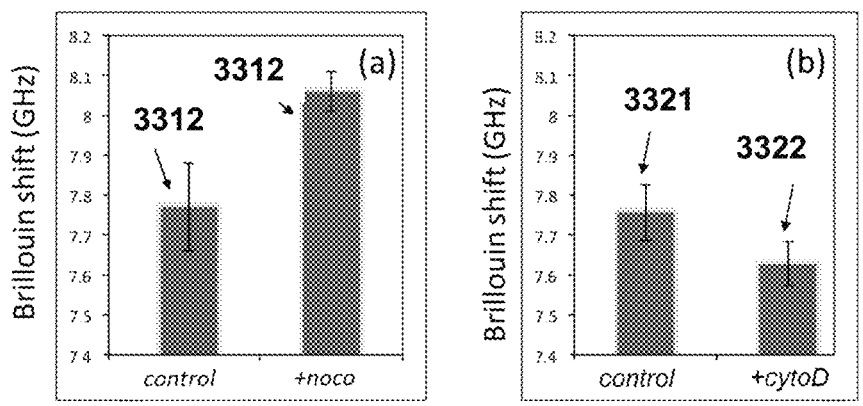
FIGS. 33A-33B illustrate exemplary results of first embodiment of this invention. It shows that inhibition of actin filament will soften the nucleus. Instead, inhibition of microtubules filament will stiffen the nucleus.

Two drugs, cytochalasin D (cytoD) and nocodazole (Noco), were applied to 3T3 cells to inhibit the actin filament and microtubules filament, respectively. NIH 3T3 fibroblast cells purchased from American Type Culture Collection (ATCC) were used for all experiments. Cells were cultured following standard protocols. For inhibitation of microtubules filament, cells were first treated by Noco of 1 ug/mL for 30 minutes, and then harvested by trypsinization and re-suspended in a solution of phosphate-buffered saline (PBS) without $Mg^{2+}$ and $Ca^{2+}$ at a concentration of ~0.1 million cells per ML before measurement. Due to the low concentration, few cells were captured by flowing. Instead, a single cell in suspension was imaged after it was delivered into the microfluidic devices. As shown in FIG. 33A, the bar plot 3311 and 3312 represent the averaged Brillouin shift of the nucleus of control and treated cell, respectively. The Brillouin shift of the treated cell 3312 is 0.29 GHz higher, indicating a distinct stiffening of its nucleus. Considering the sensitivity of the instrument is ~0.01 GHz, microtubules filament-inhibited cells were easily identified from normal cells based on the mechanical stiffening of the nucleus.

For inhibition of actin filament, cells were first treated by cytoD of 2 ug/mL for 10 minutes, and then harvested by trypsinization and re-suspended in a solution of phosphate-buffered saline (PBS) without $Mg^{2+}$ and $Ca^{2+}$ at a concentration of ~1 million cells per mL before measurement. Using the Brillouin-based label-free flow cytometry, 368 cells were acquired from the control group and 232 cells were acquired from the treated group, respectively. FIG. 33B shows the measured results, and the bar plot 3321 and 3322 represent the averaged Brillouin shift of the nucleus of the control group and treated group, respectively. The treated group 3322 features a distinct decrease of 0.12 GHz comparing with control group 3321, indicating the softening of the nucleus due to the disruption of the actin filament.

Identification of Malignant Cells

Figure 34:
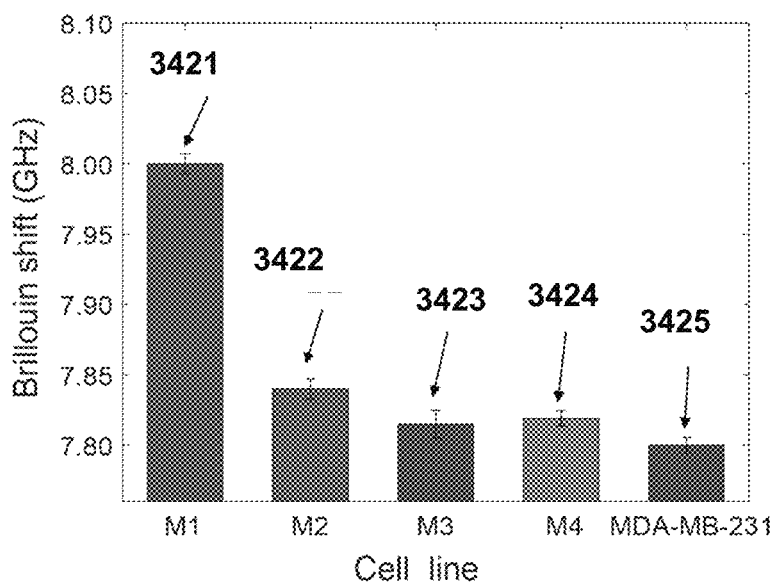
FIG. 34 illustrates exemplary results of second embodiment of this invention. It shows that nuclear mechanics can be used to grade the cancer progression.

FIG. 34 shows the second exemplary embodiment. Using Brillouin-based label-free flow cytometry five cancer-related cell lines were tested. Four of them (M1, M2, M3, and M4, obtained from the Barbara Ann Karmanos Institute) are isogenic, and increasingly tumorigenic cell lines that were derived from the MCF10A cell line, which is a standard approach to model the human breast cancer progression (Santner et al., Breast Cancer Res Treat. 65, 101-110 (2001)). The fifth is a highly metastatic breast cancer cell line MDA-MB-231 (obtained from ATCC). MCF10A (M1) is a human, epithelial, non-tumorigenic cell line. MCF10AT1k.cl2 (M2) is a pre-malignant cell that creates persistent localized benign lesions when injected into mice. MCF10CA1h (M3), and MCF10CA1a.cl1 (M4) cells have the ability to metastasize to distant lungs when they are injected into the tail vein of the mice. Experiments also indicate that M4 cells metastasize faster than the M3 cell line because it can form a faster growing tumor (Santner et al. (2001)).

All cell lines were cultured according to the standard protocols. They were grown in the same medium—standard complete medium for MCF10A cell line (M1-M4). The cells were harvested from the culture with a low concentration trypsin, resuspended them in PBS without $Mg2^+$ and $Ca2^+$ at a concentration of ~2 million cells per mL before the experiment. 223, 343, 233, 538, and 430 cells were collected from cell lines M1-M4, and MDA-MB-231, and the averaged nuclear stiffness are shown as bar plot 3421, 3422, 3423, 3424, and 3425, respectively. Bar plots 3421, 3422 show that the localized tumor M2 cell line can be clearly separated from the non-tumorigenic cell line M1 based on the difference of Brillouin frequency shift (0.16 GHz). Moreover, the bar plots 3423, 3424 and 3425 show that the metastatic cell lines M3, M4 and MDA-MB-231 can also be separated from both non-metastatic M1 and localized M2 with statistically significant difference (p value <0.01). A statistically significant difference between the M3 and M4 was not found, since their Brillouin shift measurements were similar to each other. However, a statistically significant difference (p value <0.01) was found between M3(M4) and MDA-MB-231. Based on the measurement of the mechanical signature of the nucleus, normal cells and benign lesion cells were separated from malignant cancer cells, and thus cancer progression can be graded.

Identification of Lamin Expression in Cells

FIG. 35 shows the third exemplary embodiment of this invention. One of the major structural components of the nucleus is a group of proteins known as the lamins. As the major components of the nuclear lamina, Lamin A/C conveys multiple functions, such as structural support of the nucleus, facilitate chromatin organization, gene regulation and DNA replication and repair (Ho and Lammerding, J Cell Sci. 125, 2087-2093 (2012)). Lamins are also found to link to a wide range of human diseases. For example, evidence from more than 10 cancer types suggests that lamins either play a role in cancer progression or alter in response to it (Irianto et al., Cell Mol Bioeng. 9, 258-267 (2016)). It also found out that mutations in the A-type lamins are responsible for aging diseases such as Hutchinson-Gilford progeria syndrome (HGPS) (Mounkes and Stewart, Current Opinion In Cell Biology. 16, 322-327(2004) (Butin-Israeli, Trends Genet. 28(9):464-71 (2012)). Moreover, experiments have shown that overexpression of Lamin A/C will enhance the stiffness of the nucleus while knockdown make it less stiff (Pajerowski et al., Proc Natl Acad Sci USA 104, 15619-15624 (2007); Lammerding et al., J Biol. Chem. 281, 25768-25780 (2006); Davidson (2014); Schape et al., Biophys. J 96, 4319-4325 (2009); Swift et al., Science 341, 1240104 (2013)).

Testing was performed to confirm that the sensitivity needed to measure mechanical changes in the nucleus that occur by tuning lamin expression was possible using this method, so that it can be used for cell classification. To do so, NIH/3T3 cells were cultured, and a commercial lipid-based transfection reagent (Dharmafect) was used to selectively knockdown lamin A/C expression. Solutions of Dharmafect and siRNA were complexed beforehand, then cells were incubated in media containing the transfection complex. Two commercially available siRNAs were used, one known to target lamin A/C and one scramble sequence with no known cellular target. For the one targeting lamin A/C, two different doses (25 nM and 50 nM) were used to achieve low-efficiency and high-efficiency knockdown, respectively. A control that was not subjected to transfection was also included. After a 72 hour incubation, cells were harvested by trypsinization and immediately analyzed using the label-free Brillouin-based flow cytometry set up. 122, 195, 208, 114 cells were collected for control, scrambled control, low-efficiency knockdown, and high-efficiency knockdown, as shown in the bar plots of 3512, 3522, 3532, 3542 of FIG. 35, respectively. The nuclear mechanical properties were almost unchanged (less than 0.01 GHz) in the scrambled control group 3522, compared to the non-transfected control group 3512, while a noticeable decreases (0.04 GHz and 0.07 GHz) in stiffness was observed in samples transfected with siRNA targeting lamin A/C, as shown in bar plot 3532 and 3542 of FIG. 35. On the other hand, the stiffness of the cytoplasm remain unaffected, as shown in the bar plots of 3511, 3521, 3531, and 3541.

To visualize lamin A/C expression in parallel, immunocytochemistry was performed following a standard protocol. Adherent cells were fixed with neutral buffered formalin after the 72 hour transfection described above, permeabilized with Triton-X 100, blocked with a solution of bovine serum albumin, incubated overnight with a primary anti-lamin antibody, and finally incubated briefly with a fluorophore-conjugated secondary antibody, rinsing the samples three times with PBS between each step. Fluorescent images were taken of each sample with constant imaging conditions (light intensity, exposure time). As shown in FIG. 36, fluorescent intensity of knockdown group in FIG. 36B is much weaker than that of scrambled group in FIG. 36A, indicating that lamin A/C expression was knocked down in the sample treated with lamin A/C targeting siRNA compared to the scramble siRNA sample. To roughly quantify lamin A/C knockdown, nuclear protein extracts were taken from all samples after transfection.

In one embodiment, there is provided a method for determining a mechanical property of a nucleus of at least one cell in a sample comprising acquiring the at least one cell's mechanical signatures using label-free cytometry enabled by Brillouin spectroscopy; and classifying cells based on the cells mechanical signatures of the at least one nuclei. In some embodiments, the label-free cytometry comprises any of the series of steps as provided herein using Brillouin scanning. In certain embodiments, the label-free cytometry comprises the steps of illuminating the sample by a light beam along a first direction; collecting a Brillouin scattered light emitted from the sample in response to the illuminating light beam; sending the Brillouin scattered light to an optical arrangement to induce a spectral dispersion and to a detection unit to generate a spatio-spectral pattern of the Brillouin scattered light, wherein the optical arrangement and the detection unit are positioned along a second direction; detecting the spatio-spectral pattern of the Brillouin scattering light onto the detection unit, wherein multiple points of the sample along the illuminating light beam are measured simultaneously; wherein at least one of the multiple points of the sample is a cell nucleus; calibrating the spectral pattern at each spatial point at the detection unit; and calculating the one or more Brillouin metrics at each measured sample point based on the detected spatio-spectral pattern. In some embodiments, the angle between the first direction and the second direction is any angle greater than 0°. In another embodiment, the optical arrangement to induce a spectral dispersion includes a virtually imaged phased array (VIPA), a Fabry-Perot etalon, or an echelle grating. In other embodiments, the optical arrangement induces a spectral dispersion further comprises optical elements to modify size, shape, and/or angular spread of the spatio-spectral pattern in an optical path from the sample to the detection unit.

In further embodiments, the sample is a biological sample including biological organism, tissue, or biological cells including living cells. In another embodiment, the biological cells are suspended, adherent to 2D substrates, cultured within 3D extracellular matrices, or flows through one or more channels of a microfluidic chip. In some embodiments, the at least one cell is a living eukaryotic cells. In another embodiment, the classification is based on either cell population or single cell.

In some embodiments, the Brillouin metrics are selected from the group consisting of: Brillouin frequency shift, Brillouin spectrum line width, Brillouin gain or loss spectrum, and a combination thereof. In further embodiments, the Brillouin metrics provide information regarding the mechanical properties of the cell nucleus. In other embodiments, the mechanical property of the nucleus is elasticity, viscosity, and nuclear stiffness. In some embodiments, the scanned cell is classified based on the nucleus' measured mechanical property. In another embodiment, the scanned cell is classified as a cancer cell.

In another embodiment, there is provided a system for use in the method of determining a mechanical property of a nucleus of at least one cell in a sample. In one embodiment, the system provides label-free cytometry enabled by Brillouin spectroscopy. In a further embodiment, the system obtains one or more Brillouin metrics associated with a Brillouin scattering spectrum at multiple points, wherein a least one point is within a nucleus of at least one cell in a sample. In a further embodiment, the system comprises an illumination source illuminating the sample by a light beam along a first direction, one or more lenses collecting a Brillouin scattered light emitted from the sample in response to the illuminating light beam, an optical arrangement to receive the Brillouin scattered light from the one or more lenses, the optical arrangement to induce a spectral dispersion, a detection unit to detect a spatio-spectral pattern of the Brillouin scattered light, wherein the one or more lenses, the optical arrangement, and the detection unit are positioned along a second direction, wherein multiple points of the sample along the illuminating light beam are measured simultaneously, a processor executing instructions for (1) calibrating the spectral pattern at each spatial point at the detection unit; and (2) calculating the one or more Brillouin metrics at each measured sample point based on the detected spatio-spectral pattern.

In another embodiment, the system obtains one or more Brillouin metrics including Brillouin frequency shift, Brillouin spectrum line width, Brillouin gain or loss spectrum, and a combination thereof. In a further embodiment, the one or more Brillouin metrics determine a mechanical property of at least one cell nucleus, wherein the mechanical property is selected from the group comprising elasticity, viscosity, and nuclear stiffness. In another embodiment, the scanned cell is classified based on the nucleus' measured mechanical property. In a further embodiment, the scanned cell is classified as a cancer cell.

In a further embodiment, there is provided a method of identifying a cancerous cell in a sample. In one embodiment, the method comprises determining properties of a cell nucleus using label-free cytometry as provided herein. In some embodiments, the method comprises illuminating the sample by a light beam along a first direction; collecting a Brillouin scattered light emitted from the sample in response to the illuminating light beam; sending the Brillouin scattered light to an optical arrangement to induce a spectral dispersion and to a detection unit to generate a spatio-spectral pattern of the Brillouin scattered light, wherein the optical arrangement and the detection unit are positioned along a second direction; detecting the spatio-spectral pattern of the Brillouin scattering light onto the detection unit, wherein multiple points of the sample along the illuminating light beam are measured simultaneously; wherein at least one of the multiple points of the sample is a cell nucleus; calibrating the spectral pattern at each spatial point at the detection unit; and calculating the one or more Brillouin metrics at each measured sample point based on the detected spatio-spectral pattern; and, identifying cancerous cells present in the sample by comparing the calculated Brillouin metrics to those of normal cells.

In some embodiments, the one or more Brillouin metric provide information regarding a mechanical property of the nucleus. In another embodiment, the mechanical property is selected from the group comprising elasticity, viscosity, and nuclear stiffness. In some embodiments the cancerous cells are identified by comparing the nuclear stiffness to that of non-cancerous cells.

In further embodiments, the sample is a biological sample including biological organism, tissue, or biological cells including living cells. In another embodiment, the biological cells are suspended, adherent to 2D substrates, cultured within 3D extracellular matrices, or flows through one or more channels of a microfluidic chip. In some embodiments, the at least one cell is a living eukaryotic cells. In another embodiment, the classification is based on either cell population or single cell.

In another embodiment, there is provided a method of determining whether a cell has suppressed lamin A/C expression. In a further embodiment, the method comprises acquiring at least one cells' nucleus' mechanical signature using label-free cytometry enabled by Brillouin spectroscopy. In a further embodiment, the cells are classified as having normal or suppressed lamin A/C expression based on the cells mechanical signatures of nuclei. In another embodiment, the label-free cytometry is performed as described herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for determining a mechanical property of a nucleus of at least one cell in a sample comprising:
   acquiring the at least one cell's mechanical signatures using label-free cytometry enabled by Brillouin spectroscopy; and
   classifying cells based on the cells mechanical signatures of the at least one nuclei.

2. The method of claim 1, wherein the label-free cytometry comprises the steps of:
   illuminating the sample by a light beam along a first direction;
   collecting a Brillouin scattered light emitted from the sample in response to the illuminating light beam;
   sending the Brillouin scattered light to an optical arrangement to induce a spectral dispersion and to a detection unit to generate a spatio-spectral pattern of the Brillouin scattered light, wherein the optical arrangement and the detection unit are positioned along a second direction;
   detecting the spatio-spectral pattern of the Brillouin scattering light onto the detection unit, wherein multiple points of the sample along the illuminating light beam are measured simultaneously; wherein at least one of the multiple points of the sample is a cell nucleus;
   calibrating the spectral pattern at each spatial point at the detection unit; and calculating the one or more Brillouin metrics at each measured sample point based on the detected spatio-spectral pattern.

3. The method of claim 2, wherein the one or more Brillouin metrics are selected from the group consisting of: Brillouin frequency shift, Brillouin spectrum line width, Brillouin gain or loss spectrum, and a combination thereof.

4. The method of claim 2, wherein the angle between the first direction and the second direction is any angle greater than 0°.

5. The method of claim 2, wherein the optical arrangement to induce a spectral dispersion includes a virtually imaged phased array (VIPA), a Fabry-Perot etalon, or an echelle grating.

6. The method of claim 2, wherein the optical arrangement to induce a spectral dispersion further comprises optical elements to modify size, shape, and/or angular spread of the spatio-spectral pattern in an optical path from the sample to the detection unit.

7. The method of claim 1, wherein the sample is a biological sample including biological organism, tissue, or biological cells including living cells.

8. The method of claim 7, wherein the biological cells are suspended, adherent to 2D substrates, cultured within 3D extracellular matrices, or flows through one or more channels of a microfluidic chip.

9. The method of claim 1, wherein the mechanical property of the nucleus is selected from the group comprising elasticity, viscosity, and nuclear stiffness.

10. The method of claim 9, wherein the scanned cell is classified based on the nucleus' measured mechanical property.

11. The method of claim 10, wherein the scanned cell is classified as a cancer cell.

12. The method of claim 1, wherein the at least one cell is a living eukaryotic cells.

13. The method of claim 1, wherein the classification is based on either cell population or single cell.

14. The method of claim 1, wherein the at least one cell is
(i) flowing inside a microfluidic channel,
(ii) immobilized in suspension, or
(iii) encapsulated in droplets of 3D gels.

15. A system for obtaining one or more Brillouin metrics associated with a Brillouin scattering spectrum at multiple points, wherein a least one point is within a nucleus of at least one cell in a sample, the system comprising:
an illumination source illuminating the sample by a light beam along a first direction;
one or more lenses collecting a Brillouin scattered light emitted from the sample in response to the illuminating light beam;
an optical arrangement to receive the Brillouin scattered light from the one or more lenses, the optical arrangement to induce a spectral dispersion;
a detection unit to detect a spatio-spectral pattern of the Brillouin scattered light, wherein the one or more lenses, the optical arrangement, and the detection unit are positioned along a second direction, wherein multiple points of the sample along the illuminating light beam are measured simultaneously;
a processor executing instructions for:
calibrating the spectral pattern at each spatial point at the detection unit; and
calculating the one or more Brillouin metrics at each measured sample point based on the detected spatio-spectral pattern.

16. The system of claim 15 wherein the one or more Brillouin metrics are selected from the group consisting of: Brillouin frequency shift, Brillouin spectrum line width, Brillouin gain or loss spectrum, and a combination thereof.

17. The system of claim 16, wherein the one or more Brillouin metrics determine a mechanical property of the at least one nucleus, wherein the mechanical property is selected from the group comprising elasticity, viscosity, and nuclear stiffness.

18. The system of claim 17, wherein the scanned cell is classified based on the nucleus' measured mechanical property.

19. The system of claim 18, wherein the scanned cell is classified as a cancer cell.

20. The system of claim 15, wherein the second direction is orthogonal to the first direction.

21. A method of identifying a cancerous cell in a sample, comprising:
illuminating the sample by a light beam along a first direction;
collecting a Brillouin scattered light emitted from the sample in response to the illuminating light beam;
sending the Brillouin scattered light to an optical arrangement to induce a spectral dispersion and to a detection unit to generate a spatio-spectral pattern of the Brillouin scattered light, wherein the optical arrangement and the detection unit are positioned along a second direction;
detecting the spatio-spectral pattern of the Brillouin scattering light onto the detection unit, wherein multiple points of the sample along the illuminating light beam are measured simultaneously; wherein at least one of the multiple points of the sample is a cell nucleus;
calibrating the spectral pattern at each spatial point at the detection unit; and calculating the one or more Brillouin metrics at each measured sample point based on the detected spatio-spectral pattern;
identifying cancerous cells present in the sample by comparing the calculated Brillouin metrics to those of normal cells.

22. The method of claim 21, wherein the one or more Brillouin metric provide information regarding a mechanical property of the nucleus, wherein the mechanical property is selected from the group comprising elasticity, viscosity, and nuclear stiffness.

23. The method of claim 21, wherein the second direction is orthogonal to the first direction.

* * * * *